US007223364B1

(12) United States Patent
Johnston et al.

(10) Patent No.: US 7,223,364 B1
(45) Date of Patent: May 29, 2007

(54) DETECTION ARTICLE HAVING FLUID CONTROL FILM

(75) Inventors: Raymond P. Johnston, Lake Elmo, MN (US); Patrick R. Fleming, Lake Elmo, MN (US); Kurt J. Halverson, Lake Elmo, MN (US); James G. Bentsen, North St. Paul, MN (US); Gary E. Krejcarek, White Bear Lake, MN (US); Koichi Sano, Sagamihara (JP)

(73) Assignee: 3M Innovative Properties Company, St. Paul, MN (US)

( * ) Notice: Subject to any disclaimer, the term of this patent is extended or adjusted under 35 U.S.C. 154(b) by 585 days.

(21) Appl. No.: 09/612,418

(22) Filed: Jul. 7, 2000

Related U.S. Application Data

(60) Provisional application No. 60/142,585, filed on Jul. 7, 1999.

(51) Int. Cl.
*C12M 1/14* (2006.01)
*G01N 1/10* (2006.01)

(52) U.S. Cl. .................... 422/68.1; 422/55; 422/82.05; 422/93

(58) Field of Classification Search .................. 422/50, 422/68.1, 129, 82.05; 435/4, 5, 6, 7.1, 7.2, 435/287.2; 436/501
See application file for complete search history.

(56) References Cited

U.S. PATENT DOCUMENTS 3,715,192 A 2/1973 Wenz et al.
3,993,566 A 11/1976 Goldberg et al.
4,233,029 A 11/1980 Columbus
4,259,233 A 3/1981 Carrico et al.
4,271,119 A 6/1981 Columbus
4,277,966 A 7/1981 Rambauske
4,323,069 A 4/1982 Ahr et al.
4,413,407 A 11/1983 Columbus
4,469,601 A * 9/1984 Beaver et al. .............. 210/658
4,579,555 A 4/1986 Russo
4,601,861 A 7/1986 Pricone et al.
4,639,748 A 1/1987 Drake et al.
4,668,558 A 5/1987 Barber
4,673,657 A * 6/1987 Christian .................... 436/501
4,758,481 A 7/1988 Fauvel (Continued)

FOREIGN PATENT DOCUMENTS

DE 42 10 072 A1 3/1993

(Continued)

OTHER PUBLICATIONS

Webster's II New Riverside University Dictionary [Published by Houghton Mifflin Company, One Beacon Street, Boston, Massachusetts 02108] (1984, p. 1123.*

(Continued)

*Primary Examiner*—Marjorie A. Moran
(74) *Attorney, Agent, or Firm*—Christopher D. Gram

(57) ABSTRACT

The present invention provides a detection article including at least one fluid control film layer having at least one microstructured major surface with a plurality of microchannels therein. The microchannels are configured for uninterrupted fluid flow of a fluid sample throughout the article. The film layer includes an acquisition zone for drawing the fluid sample into the plurality of microchannels at least by spontaneous fluid transport. The film layer also includes a detection zone having at least one detection element that facilitates detection of a characteristic of the fluid sample within at least one microchannel of the detection zone.

33 Claims, 16 Drawing Sheets

U.S. PATENT DOCUMENTS

| | | | | |
|---|---|---|---|---|
| 4,810,381 | A * | 3/1989 | Hagen et al. | 210/502.1 |
| 4,863,121 | A | 9/1989 | Savill | |
| 4,906,439 | A | 3/1990 | Grenner | |
| 4,913,858 | A | 4/1990 | Miekka et al. | |
| 4,950,549 | A | 8/1990 | Rolando et al. | |
| 4,986,496 | A | 1/1991 | Marentic et al. | |
| 5,061,029 | A | 10/1991 | Ishikawa | |
| 5,069,403 | A | 12/1991 | Marentic et al. | |
| 5,078,925 | A | 1/1992 | Rolando et al. | |
| 5,133,516 | A | 7/1992 | Marentic et al. | |
| 5,136,678 | A | 8/1992 | Yoshimura | |
| 5,152,060 | A | 10/1992 | Schubert et al. | |
| 5,158,557 | A | 10/1992 | Noreen et al. | |
| 5,175,030 | A | 12/1992 | Lu et al. | |
| 5,179,005 | A | 1/1993 | Phillips et al. | |
| 5,200,248 | A | 4/1993 | Thompson et al. | |
| 5,227,008 | A | 7/1993 | Klun et al. | |
| 5,249,359 | A | 10/1993 | Schubert et al. | |
| 5,265,184 | A | 11/1993 | Lebby et al. | |
| 5,286,362 | A | 2/1994 | Hoenes et al. | |
| 5,296,375 | A | 3/1994 | Kricka et al. | |
| 5,304,487 | A | 4/1994 | Wilding et al. | |
| 5,376,252 | A | 12/1994 | Ekstrom et al. | |
| 5,399,486 | A | 3/1995 | Cathey et al. | |
| 5,409,666 | A | 4/1995 | Nagel et al. | |
| 5,411,480 | A | 5/1995 | Kriesel | |
| 5,411,858 | A | 5/1995 | McGeehan et al. | |
| 5,429,807 | A | 7/1995 | Matson et al. | |
| 5,440,332 | A | 8/1995 | Good | |
| 5,445,934 | A | 8/1995 | Fodor et al. | |
| 5,450,235 | A | 9/1995 | Smith et al. | |
| 5,451,504 | A * | 9/1995 | Fitzpatrick et al. | 435/7.2 |
| 5,474,796 | A | 12/1995 | Brennan | |
| 5,477,239 | A | 12/1995 | Busch et al. | |
| 5,498,392 | A | 3/1996 | Wilding et al. | |
| 5,500,071 | A | 3/1996 | Kaltenbach et al. | |
| 5,514,120 | A | 5/1996 | Johnston et al. | |
| 5,529,676 | A | 6/1996 | Maley et al. | |
| 5,571,410 | A | 11/1996 | Swedberg et al. | |
| 5,585,186 | A | 12/1996 | Scholz et al. | |
| 5,601,678 | A | 2/1997 | Gerber et al. | |
| 5,602,202 | A | 2/1997 | Groves | |
| 5,635,358 | A | 6/1997 | Wilding et al. | |
| 5,637,469 | A | 6/1997 | Wilding et al. | |
| 5,641,400 | A | 6/1997 | Kaltenbach et al. | |
| 5,651,888 | A | 7/1997 | Shimizu et al. | |
| 5,658,413 | A | 8/1997 | Kaltenbach et al. | |
| 5,658,802 | A | 8/1997 | Hayes et al. | |
| 5,691,846 | A | 11/1997 | Benson, Jr. et al. | |
| 5,698,299 | A | 12/1997 | Schmidt et al. | |
| 5,705,813 | A | 1/1998 | Apffel et al. | |
| 5,707,799 | A | 1/1998 | Hansmann et al. | |
| 5,716,778 | A | 2/1998 | Weng et al. | |
| 5,716,825 | A | 2/1998 | Hancock et al. | |
| 5,721,435 | A | 2/1998 | Troll | |
| 5,726,026 | A | 3/1998 | Wilding et al. | |
| 5,728,446 | A | 3/1998 | Johnston et al. | |
| 5,737,457 | A | 4/1998 | Saini et al. | |
| 5,750,015 | A | 5/1998 | Soane et al. | |
| 5,755,942 | A | 5/1998 | Zanzucchi et al. | |
| 5,757,482 | A | 5/1998 | Fuchs et al. | |
| 5,842,787 | A | 12/1998 | Kopf-Sill et al. | |
| 5,848,769 | A | 12/1998 | Fronek et al. | |
| 5,860,626 | A | 1/1999 | Moser | |
| 5,885,470 | A | 3/1999 | Parce et al. | |
| 5,922,615 | A | 7/1999 | Nowakowski et al. | |
| 5,932,315 | A | 8/1999 | Lum et al. | |
| 5,951,836 | A | 9/1999 | McAleer et al. | |
| 5,952,173 | A | 9/1999 | Hansmann et al. | |
| 5,958,782 | A | 9/1999 | Bentsen et al. | |
| 6,080,243 | A | 6/2000 | Insley et al. | 134/21 |
| 6,238,538 | B1 | 5/2001 | Parce et al. | 204/600 |
| 6,240,790 | B1 | 6/2001 | Swedberg et al. | 73/863.21 |
| 6,290,685 | B1 | 9/2001 | Insley et al. | 604/317 |
| 6,375,871 | B1 | 4/2002 | Bentsen et al. | 264/1.6 |
| 6,416,642 | B1 * | 7/2002 | Alajoki et al. | 204/451 |
| 6,420,622 | B1 | 7/2002 | Johnston et al. | 602/41 |
| 6,431,695 | B1 | 8/2002 | Johnston et al. | 347/86 |
| 6,587,197 | B1 * | 7/2003 | Rahbar-Dehghan | 356/318 |
| 6,591,852 | B1 * | 7/2003 | McNeely et al. | 137/14 |
| 6,613,560 | B1 * | 9/2003 | Tso et al. | 435/287.2 |

FOREIGN PATENT DOCUMENTS

| | | |
|---|---|---|
| DE | 195 41 266 A1 | 5/1997 |
| GB | 1 338 579 | 11/1973 |
| GB | 1 354 502 | 5/1974 |
| WO | WO 91/12949 | 9/1991 |
| WO | WO 92/07899 | 5/1992 |
| WO | WO 92/08972 | 5/1992 |
| WO | WO 93/111727 | 6/1993 |
| WO | WO 96/04547 | 2/1996 |
| WO | WO 96/09879 | 4/1996 |
| WO | WO 96/10747 | 4/1996 |
| WO | WO 97/02357 | 1/1997 |
| WO | WO 97/13633 | 4/1997 |
| WO | WO 98/00231 | 1/1998 |
| WO | WO 98/21626 | 5/1998 |
| WO | WO 98/24544 | 6/1998 |
| WO | WO 98/46438 | 10/1998 |
| WO | WO 99/06589 | 2/1999 |
| WO | WO 99/19717 | 4/1999 |

OTHER PUBLICATIONS

Merriam-Webster Online Dictionary: definitions of “uniform” and “regular”, printed Jul. 8, 2006.*

Article: “Fabrication of Novel Three-Dimensional Microstructures by the Anisotropic Etching of (100) and (110) Silicon”, Ernest Bassous, *IEEE Transactions on Electron Devices*, vol. ED-25, No. 10, Oct. 1978.

Article: “Mictrotechnology Opens Doors to the Universe of Small Space”, Peter Zuska *Medical Device & Diagnostic Industry*, Jan. 1997.

Article: “Simple and Low Cost Fabrication of Embedded Micro-Channels by Using a New Thick-Film Photoplastic” Guerin, et al. *Digest of Technical Papers*, vol. 2, Jun. 1997.

Article: “Fabrication of Microstructures with high aspect ratios and great structural heights by synchrotron radiation lithography, galvanoforming, and plastic moulding (LIGA process)” Becker, et al. *MiMicroelectronic Engineering* 4 (1986).

Article: “For lab chips, the future is plastic”. IVD Technology Magazine, May 1997.

Article: “Microchannel Electrophoretic Separations of DNA in Injection-Molded Plastic Substrates” McCormick et al. *Analytical Chemistry*, vol. 69, No. 14, Jul. 1997.

Article: “Processing of Three-Dimensional Microstructures Using Macroporous n-Type Silicon” Ottow et al. *J. Electrochem. Soc.*, vol. 143, No. 1, Jan. 1996.

Article: “UV Laser Machined Plymer Substrates for the Development of Microdignostic Systems” Roberts, et al. *Analytical Chemistry*, vol. 69, No. 11, Jun. 1997.

English Translation of Opponent’s Letter Dated Mar. 6, 2006, Opposition Against European Patent EP 1 196 243 B1, (10 pages).

Response to Notice of Opposition dated Oct. 24, 2005 from Vossius & Partner Regarding Communication dated Apr. 14, 2006 and the Notice of Opposition filed on behalf of Roche Diagnostics GmbH for EP 00947111.1 (9 pages).

English Translation of the Notice of opposition filed by Roche Diagnostics GmbH on Mar. 7, 2005, (20 pages), Opposition against Patent EP 1 196 243.

* cited by examiner

Fig. 1a
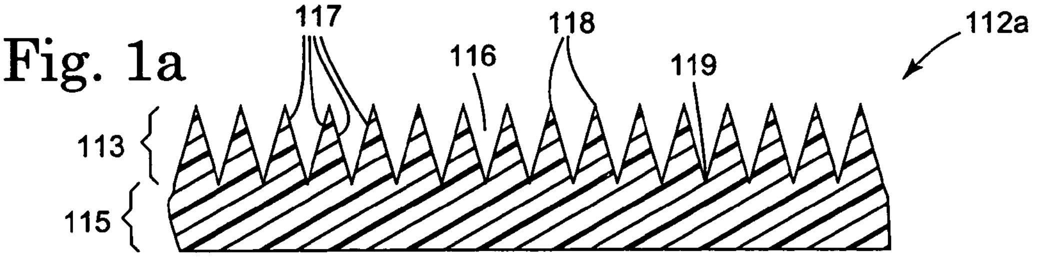
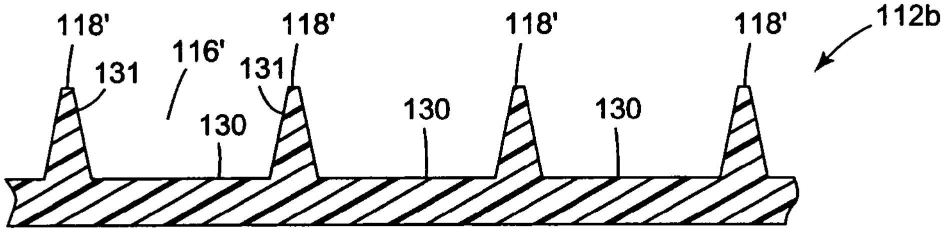
Fig. 1b
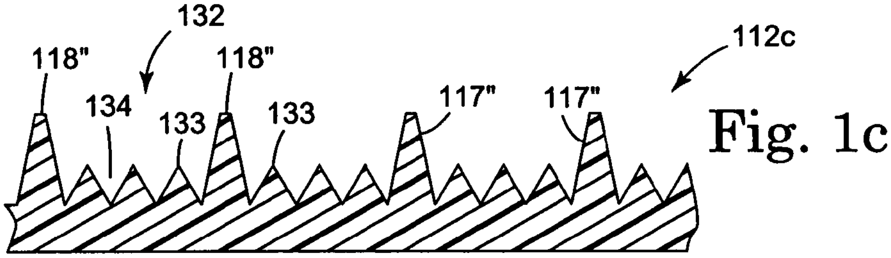
Fig. 1c
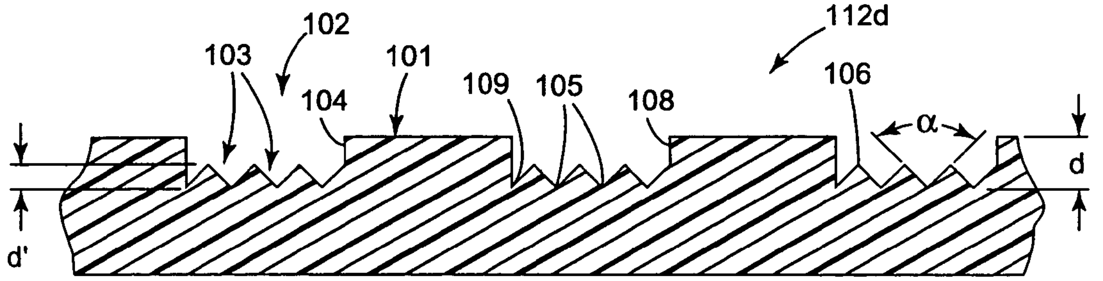
Fig. 1d

Fig. 2a
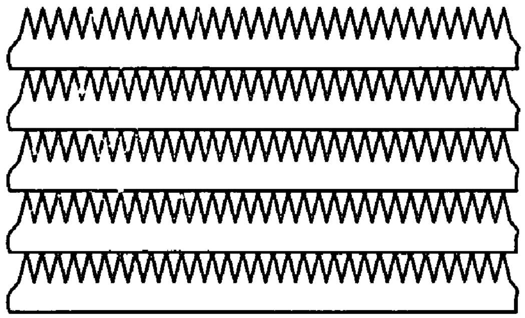
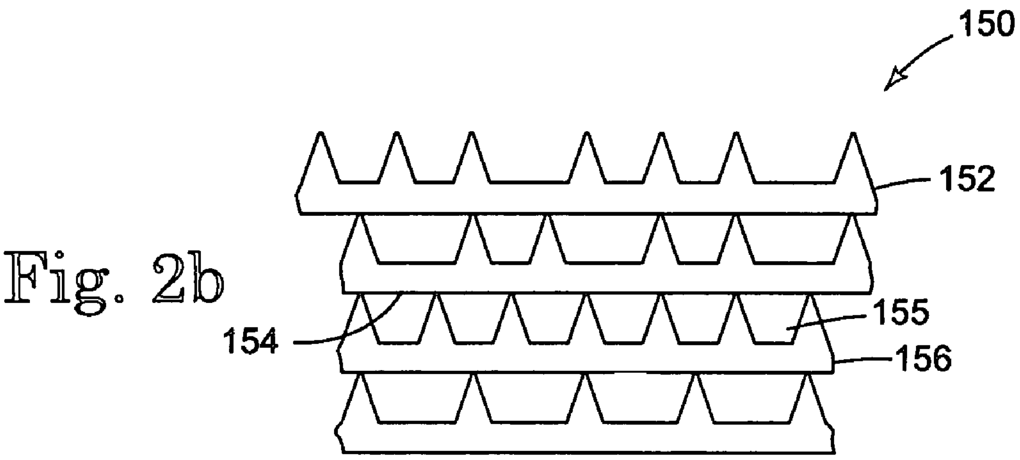
Fig. 2b
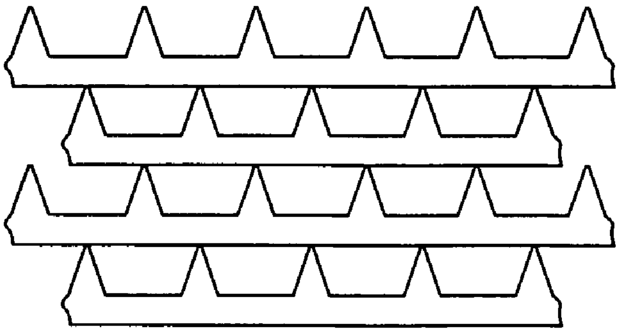
Fig. 2c

DETECTION ARTICLE HAVING FLUID CONTROL FILM

This application claims priority to U.S. provisional application Ser. No. 60/142,585, filed on Jul. 7, 1999 and entitled Detection Article Having Fluid Control Film.

FIELD OF THE INVENTION

This invention relates to articles that have the capability to control or transport fluids, especially biological fluids. In particular, this invention relates to articles that have the capability for acquisition and transport of such fluids for subsequent detection purposes.

BACKGROUND OF THE INVENTION

Biological assays that require sample partitioning are traditionally performed in test-tubes or microwell arrays and require manual intervention at several stages to enable the sampling, purification, reagent addition, and detection steps required to make the assay selective and specific. Ongoing developments in this field have focused on the ability to rapidly process fluid samples in order to increase efficiency and cost effectiveness. In some cases, automated sample handling equipment has been developed to reduce the amount of manual intervention and to assist in the detection of assay reaction products in multiple microwells of an array, thereby increasing the speed and efficiency of fluid sample testing, handling and preparation. However, because of the bulk of the automated equipment, these tests are often difficult to perform in the field.

In addition to these developments, there has been a drive towards reduction in size of the instrumentation used for analysis and manipulation of the samples. This reduction in size offers several advantages in addition to increased analytical speed, such as the ability to analyze very small samples, the ability to use reduced amount of reagents and a reduction in overall cost.

An outgrowth of these size reductions is an increased need for accuracy in the quantity of fluid sample provided. With volumes in the micro-liter range, even miniscule variations in sample quantity may have a significant impact on the analysis and results of the fluid sample tests. As a result, articles used to house the fluid samples during preparation, handling, testing and analysis are required that provide extremely accurate fluid containment and fluid transport structures on or in the articles. Highly accurate articles for microfluid handling and analysis have been produced from glass or silicon substrates having lithographically patterned and etched surface features. Using lithographically patterned glass or silicon based microfluidic chips, fundamental feasibility has been established for microfluidic chip based enzyme assays, immunoassays, DNA hybridization assays, particle manipulations, cell analysis and molecular separations. However, there remains a need in the art to combine these various functions to support complex biological assay tasks important to biomedical R&D, pharmaceutical drug discovery, medical diagnostics, food and agricultural microbiology, military and forensic analysis. Glass and silicon based chips pose several practical problems to reaching these objectives. These problems relate to the high cost of manufacture, incompatibilities between discrete processes for microfabrication of the glass substrates and continuous processes for incorporating the assay reagents, and the difficulties associated with sealing a glass cover onto the reagent impregnated chip. Articles formed from plastic substrates, such as polyimides, polyesters and polycarbonates, have been proposed as well.

Size reductions in the field have also produced a need for devices and methods for introducing fluid sample into the highly accurate fluid containment and transport structures. Some current methods include dispensing of the fluid sample via one or more pipettes, syringes, or other similar devices. This mechanical introduction of a fluid sample requires accurate alignment between the fluid dispensing device and the test device, as well as accurate metering of the amount of fluid sample dispensed.

In order to accommodate the need for high throughput analysis systems (both automated and manual), substrates provided with a plurality of fluid sample handling and analysis articles have been developed. Such substrates may be formed as flexible rolled goods that allow simultaneous and/or synchronous testing of fluid samples contained in the plurality of articles. Alternatively, such substrates may be formed as rigid, semi-rigid or flexible sheet goods which also may allow for simultaneous and/or synchronous testing of the fluid samples housed therein. Optionally, articles may be detached from the roll or sheet provided goods to accommodate limited testing.

There is an ongoing need for efficient, cost effective and rapid testing of fluid samples, especially in the area of biological detection assays as described above, coupled with a requirement for accuracy in fluid quantities and article structures. This combination has produced a corresponding need for manufacturing and formation methods which produce the required fluid testing articles in a cost effective and efficient manner while maintaining accuracy within a particular article, and from article to article. In addition, an ongoing requirement exists for fluid testing article designs that meet the various fluid handling, testing and analyzing needs of the diagnostic, forensic, pharmaceutical and other biological analysis industries, which adhere to the strict requirements of efficiency, cost effectiveness and accuracy described above while also simplifying the testing and analysis processes. Furthermore, it would be advantageous to provide a fluid handling architecture that partitions a sample into aliquots, each aliquot to be reacted with a different combination of assay reagents. It would also be advantageous to provide a fluid handling architecture with additional optical or electronic features that enhance the detection of fluorogenic or chromogenic indicators, electrochemical reagents, agglutination reagents and the like.

SUMMARY OF THE INVENTION

The detection article of the present invention meets the needs of the fluid sample testing industry by providing for the efficient and rapid handling of fluid samples for the purposes of conducting biological assays. The present invention provides novel miniaturized detection articles that include coextensive channels providing uninterrupted fluid flow along the length of the article, wherein the channels acquire a fluid sample, transport the fluid sample along the channels, and facilitate detection relating to the fluid sample within the channels. The present invention also includes methods of using and making these articles.

In at least one embodiment of the present invention, a detection article includes at least one fluid control film component having at least one microstructure-bearing surface including a plurality of coextensive channels therein. The detection article at least includes a detection zone, wherein the detection zone provides for the detection of a characteristic of the fluid sample within the detection zone, including but not limited to a result of an event or a condition within one or more of the channels. The detection zone includes at least one detection element, which is any composition of matter or structural member that facilitates detection of the characteristic. Facilitation of detection is meant to encompass any involvement in the detection process and/or any modification of the fluid sample for the purposes of enabling detection. The detection elements may be located in the channels, in an optional cap layer covering or partially covering the channels, or may be external to the article.

The detection article also includes an acquisition zone that serves as an interface between the liquid sample and the detection article. The acquisition zone preferably includes two or more channels that are capable of wicking a fluid sample into the article by spontaneous liquid transport, and thus must be suitably hydrophilic and must additionally be provided with an appropriate surface energy level if the channels are open and not covered by a cap layer.

In another embodiment, the detection article includes a three dimensional array of coextensive channels formed from a multi-layer stack of fluid control film layers. The stacked fluid control film layers may be used as a multi-parameter detection article, wherein the individual channels of the stacked array may contain unique detection elements.

The methods of the present invention include using the detection articles for glucose monitoring, enzyme-based testing, bacterial identification, antibody probe capture, characterization of biological macromolecules, DNA microarrays, sterilization assurance and numerous other biological assays. The methods of the present invention also include making the detection articles by continuous roll-to-roll processes. This enables the incorporation of high aspect ratio microreplicated channels with substructures such as nested channels to enhance flow dynamics and variable aspect ratios to control fluid flow timing or optical path-lengths. In addition, continuous processes provide for the patterning of organic or inorganic thin films to control surface energy and chemical absorption, the patterning of sample purification elements, assay reagent elements, microptical and flex circuit elements.

The present invention provides many benefits and advantages over prior art fluid sample testing devices, including precise control of fluid flow within the detection article, thus allowing for rapid fluid acquisition and distribution, as well as three dimensional flow control. The fluid streams within the article may be split and then re-associated if desired, and then re-split in a different manner, as needed, thus allowing for novel multiplexed tests. In addition, multiple layer articles may be provided with apertures fluidly connecting layers together.

Additionally, use of an open microstructure surface allows for easy placement of surface agents into desired regions to modify the fluid or to facilitate detection. Highly multi-plexed, miniaturized detection articles may be prepared by placing different detection elements into adjacent channels of the article, thereby facilitating detection of different results in each channel or detection of different levels or concentrations of the same result. Using an impermeable material to create the microstructure allows for the potential of an open dip stick without a protective cover, wherein the fluid sample may be held in the channels via surface tension, which can be a very strong retaining force. On the other hand, use of a semi-permeable material to create the microstructure would allow for controlled fluid diffusion to be employed. Optionally, a cap or cover layer may be provided, which may serve as a protective layer, may increase the wicking ability of the acquisition zone and/or may facilitate detection.

The fluid transport nature of the microstructured fluid control film layers used to form the detection articles of the present invention allows for the easy introduction of fluid sample into the structure through capillary action, without the need for additional processes such as sample input by syringe or pipetting. This feature makes the detection article faster and easier to use, cheaper to manufacture and use, and generally more versatile. The present invention also provides an ability to further process the film layer, such as by laminating a cap layer onto the film layer, forming multiple layer articles, and/or forming other structures.

Additional benefits include the ability to facilitate detection by observation or viewing of the detection zone through the provision of open channels, windows or optically transparent cap layers. Optical transmission through a microstructured cap layer or a fluid control film layer may be improved through the canting of the angles of the channels provided in the microstructured surface, or by other means.

BRIEF DESCRIPTION OF THE SEVERAL VIEWS OF THE DRAWINGS

FIG. 1*a* is a cross-sectional view of a microstructured fluid control film having V-shaped channels.

FIG. 1*b* is a cross-sectional view of a microstructured fluid control film having trapezoidal channels with a flat base.

FIG. 1*c* is a cross-sectional view of a microstructured fluid control film having trapezoidal channels with multiple V-shaped sub-channels formed in the base.

FIG. 1*d* is a cross-sectional view of a microstructured fluid control film having substantially rectilinear channels with V-shaped sub-channels.

FIG. 2*a* is an end view of multiple stacked layers of fluid control film wherein each layer includes the same configuration of microstructured channels.

FIG. 2*b* is an end view of multiple stacked layers of fluid control film wherein each layer includes different configurations of microstructured channels.

FIG. 2*c* is an end view of multiple stacked layers of fluid control film wherein the channels of adjacent layers are staggered.

DEFINITIONS

Figure 1E:
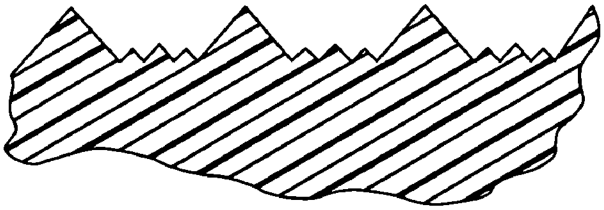
FIG. 1*e* is a cross-sectional view of a microstructured fluid control film having V-shaped channels with multiple V-shaped sub-channels.
Figure 1F:
FIG. 1*f* is a cross-sectional view of a microstructured fluid control film having concave channels with V-shaped sub-channels.
Figure 1G:
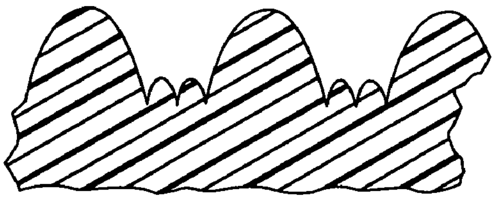
FIG. 1*g* is a cross-sectional view of a microstructured fluid control film having convex channels and multiple convex sub-channels.
Figure 1H:
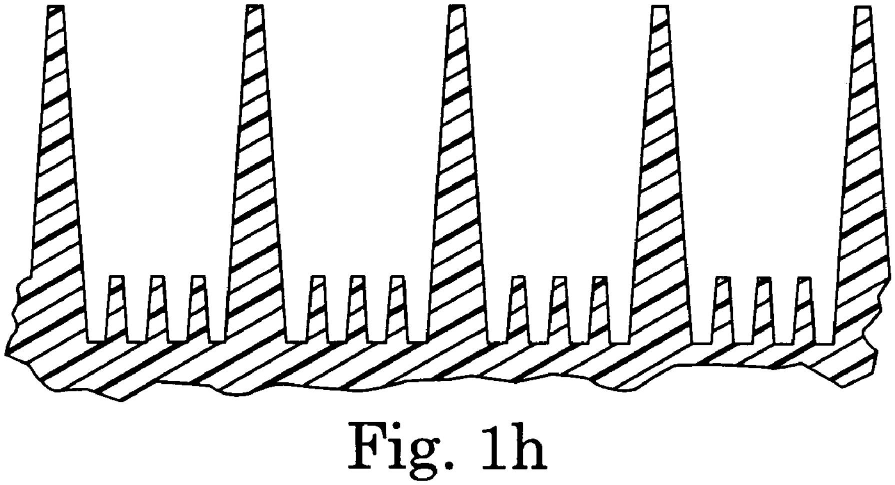
FIG. 1*h* is a cross-sectional view of a microstructured fluid control film having trapezoidal steep-walled channels with trapezoidal sub-channels.

Fluid Control Film ("FCF") refers to a film or sheet or layer having at least one major surface comprising a microreplicated pattern capable of manipulating, guiding, containing, spontaneously wicking, transporting, or controlling, a fluid.

Fluid Transport Film ("FTF") refers to a film or sheet or layer having at least one major surface comprising a microreplicated pattern capable of spontaneously wicking or transporting a fluid.

"Microreplication" means the production of a microstructured surface through a process where the structured surface features retain an individual feature fidelity during manufacture.

DETAILED DESCRIPTION OF THE INVENTION

With reference to the attached Figures, it is to be understood that like components are labeled with like numerals throughout the several Figures.

The present invention relates to articles that incorporate a fluid control film component. At the beginning of this section suitable fluid control films will be described generally. Descriptions of illustrative articles of the present invention incorporating these films will follow, along with specific applications of such articles.

Fluid Control Films

Suitable fluid control films for use in the present invention are described in U.S. Serial Nos. U.S. Ser. Nos. 08/905,481; 09/099,269; 09/099,555; 09/099,562; 09/099,565; 09/099,632; 09/100,163; 09/106,506; and 09/235,720; and U.S. Pat. Nos. 5,514,120; and 5,728,446, which are herein incorporated by reference. Preferred fluid control films of the invention are in the form of sheets or films having microstructured surfaces including a plurality of open channels having a high aspect ratio (that is, channel length divided by the wetted channel perimeter), rather than a mass of fibers. The channels of fluid control films usable with the invention preferably provide more effective liquid flow than is achieved with webs, foam, or tows formed from fibers. The walls of channels formed in fibers will exhibit relatively random undulations and complex surfaces that interfere with flow of liquid through the channels. In contrast, the channels in the present invention are precisely replicated, with high fidelity, from a predetermined pattern and form a series of individual open capillary channels that extend along a major surface. These microreplicated channels formed in sheets, films, or tubes are preferably uniform and regular along substantially each channel length and more preferably from channel to channel.

Fluid control films of the present invention can be formed from any thermoplastic material suitable for casting, or embossing including, for example, polyolefins, polyesters, polyamides, poly(vinyl chloride), polyether esters, polyimides, polyesteramide, polyacrylates, polyvinylacetate, hydrolyzed derivatives of polyvinylacetate, etc. Polyolefins are preferred, particularly polyethylene or polypropylene, blends and/or copolymers thereof, and copolymers of propylene and/or ethylene with minor proportions of other monomers, such as vinyl acetate or acrylates such as methyl and butylacrylate. Polyolefins are preferred because of their excellent physical properties, ease of processing, and typically lower cost than other thermoplastic materials having similar characteristics. Polyolefins readily replicate the surface of a casting or embossing roll. They are tough, durable and hold their shape well, thus making such films easy to handle after the casting or embossing process. Hydrophilic polyurethanes are also preferred for their physical properties and inherently high surface energy. Alternatively, fluid control films can be cast from thermosets (curable resin materials) such as polyurethanes, acrylates, epoxies and silicones, and cured by exposure to heat or UV or E-beam radiation, or moisture. These materials may contain various additives including surface energy modifiers (such as surfactants and hydrophilic polymers), plasticizers, antioxidants, pigments, release agents, antistatic agents and the like. Suitable fluid control films also can be manufactured using pressure sensitive adhesive materials. In some cases the channels may be formed using inorganic materials (e.g., glass, ceramics, or metals). Preferably, the fluid control film substantially retains its geometry and surface characteristics upon exposure to liquids. The fluid control film may also be treated to render the film biocompatible. For example, a heparin coating may be applied.

For purposes of this invention, a "film" is considered to be a thin (less than 5 mm thick) generally flexible sheet of polymeric material. The economic value in using inexpensive films with highly defined microstructure-bearing film surfaces is great.

Structured polymeric film layers produced in accordance with known techniques can be microreplicated. The provision of microreplicated structured layers is beneficial because the surfaces can be mass produced without substantial variation from product-to-product and without using relatively complicated processing techniques. "Microreplication" or "microreplicated" means the production of a microstructured surface through a process where the structured surface features retain an individual feature fidelity during manufacture, from product-to-product, that varies no more than about 50 micrometers. The microreplicated surfaces preferably are produced such that the structured surface features retain an individual feature fidelity during manufacture, from product-to-product, which varies no more than 25 micrometers. In accordance with the present invention, a microstructured surface comprises a surface with a topography (the surface features of an object, place or region thereof) that has individual feature fidelity that is maintained with a resolution of between about 50 micrometers and 0.05 micrometers, more preferably between 25 micrometers and 1 micrometer.

Figure 1I:
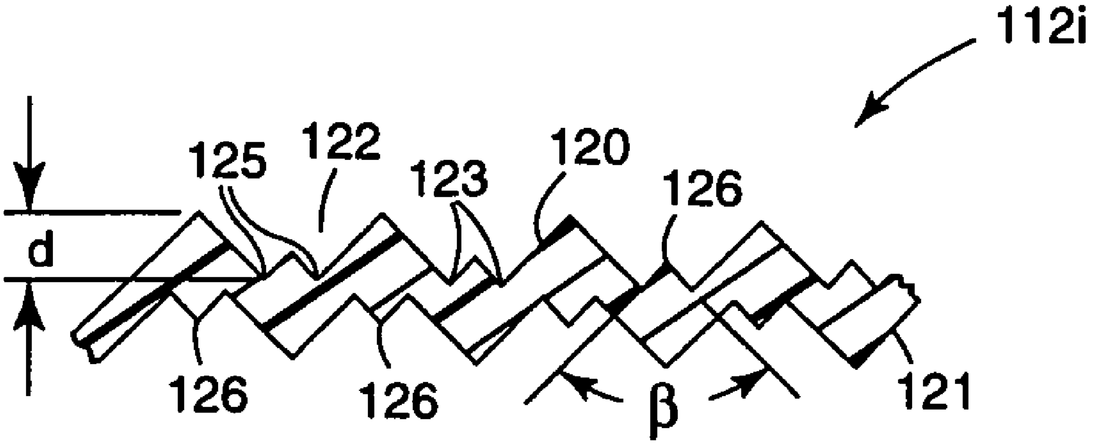
FIG. 1*i* is a cross-sectional view of a microstructured fluid control film having primary channels on both major surfaces with the channels laterally offset on each surface.
Figure 1J:
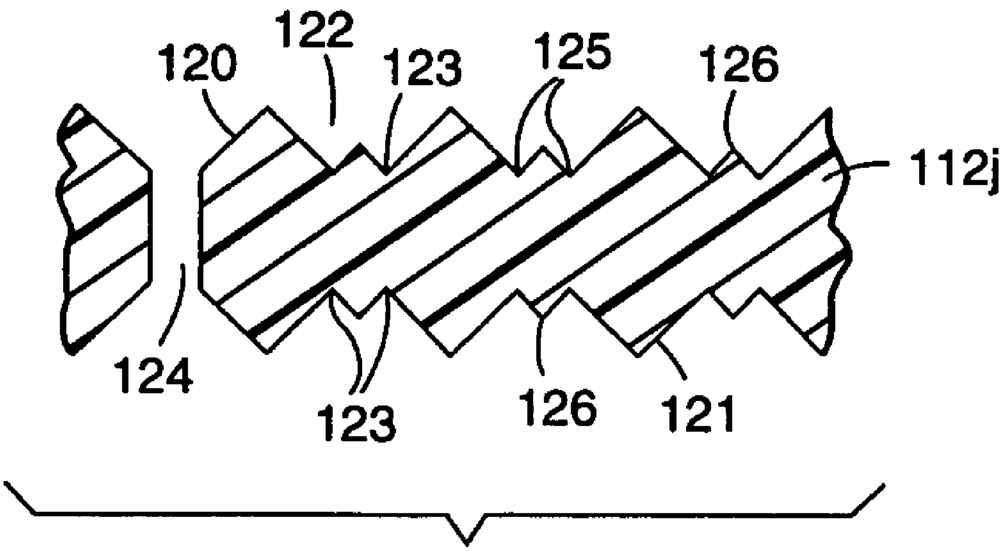
FIG. 1*j* is a cross-sectional view of a microstructured fluid control film having primary channels on both major surfaces with the channels aligned directly opposite each other on each surface.

The channels of the fluid control films of the present invention can be any geometry that provides for desired liquid transport, and preferably one that is readily replicated. In some embodiments, the fluid control film will have primary channels on only one major surface as shown in FIGS. 1*a*–1*d*. In other embodiments, however, the fluid control film will have primary channels on both major surfaces, as shown in FIGS. 1*i* and 1*j*.

As shown in FIG. 1*a*, a fluid control film layer 112*a* has a first major surface 113 and second major surface 115 wherein the first major surface 113 includes a plurality of microstructured channels 116. The channels 116 are defined within the structured surface 113 in accordance with the illustrated embodiment by a series of v-shaped sidewalls 117 and peaks 118. In some cases, the sidewalls 117 and peaks 118 may extend entirely from one edge of the layer 112*a* to another without alteration—although, in some applications, it may be desirable to shorten the sidewalls 117 and thus extend the peaks 118 only along a portion of the structured surface 113. That is, channels 116 that are defined between peaks 118 may extend entirely from one edge to another edge of the layer 112*a*, or such channels 116 may only be defined to extend over a portion of the layer 112*a*. Channels that extend only over a portion may begin at an edge of the layer 112*a*, or they may begin and end intermediately within the structured surface 113 of the layer 112*a*. The channels are defined in a predetermined, preferably ordered arrangement over a continuous surface of polymeric material.

The layer 112*a* may be utilized with the channels 116 in an open configuration, or the layer 112*a* may be utilized with a cap layer (not shown) that may be secured along one or more of the peaks 118. When used with a cap layer, the layer 112*a* defines discrete channels having relatively isolated fluid flow and containment.

As shown in FIG. 1*b*, another embodiment of a fluid control film layer 112*b* is shown including channels 116' that have a wider flat valley between slightly flattened peaks 118'. In this embodiment, bottom surfaces 130 extend between channel sidewalls 131, whereas in the FIG. 1*a* embodiment, sidewalls 117 connect together to form lines 119. Like the FIG. 1*a* embodiment, a cap layer (not shown) may be secured along one or more of the peaks 118' to define discrete channels 116'.

FIG. 1*c* illustrates another embodiment of a fluid control film layer 112*c* configured with wide channels 132 defined between peaks 118". However, instead of providing a flat surface between channel sidewalls 117", a plurality of smaller peaks 133 are located between the sidewalls 117" of the peaks 118". These smaller peaks 133 thus define secondary channels 134 therebetween. Peaks 133 may or may not rise to the same level as peaks 118", and as illustrated create a first wide channel 132 including smaller channels 134 distributed therein. The peaks 118" and 133 need not be evenly distributed with respect to themselves or each other.

FIGS. 1*e*–1*j* illustrate various alternative embodiments of the fluid control film usable with the present invention. Although FIGS. 1*a*–1*j* illustrate elongated, linearly-configured channels, the channels may be provided in other configurations. For example, the channels could have varying cross-sectional widths along the channel length—that is, the channels could diverge and/or converge along the length of the channel. The channel sidewalls could also be contoured rather than being straight in the direction of extension of the channel, or in the channel height. Generally, any channel configuration that can provide at least multiple discrete channel portions that extend from a first point to a second point within the fluid transport device are contemplated. The channels may be configured to remain discrete along their whole length if desired.

With reference to FIG. 1*d*, a preferred embodiment of a fluid control film layer 112*d* includes a channel geometry having a plurality of rectilinear primary channels 102 formed between flat lands 101. The primary channel 102 has included secondary channels 103 formed by a multitude of notches 105. The notches 105 (or secondary channels 103, where the channels are V-shaped and have substantially straight sidewalls) have an included angle, α, from about 10° to about 120°, preferably from about 10° to about 100°, and most preferably from about 20° to about 95°. The notch included angle is generally the secant angle taken from the notch to a point 2 to 1000 microns from the notch on the sidewalls forming the notch, preferably the included angle is the secant angle taken at a point halfway up the secondary channel sidewalls.

The primary channel included angle is not critical except in that it should not be so wide that the primary channel is ineffective in channeling liquid. Generally, the primary channel maximum width is less than 3000 microns and preferably less than 1500 microns. The included angle of a V-channel shaped primary channel will generally be from about 10 degrees to 120 degrees, preferably 30 to 90 degrees. If the included angle of the primary channel is too narrow, the primary channel may not have sufficient width at its base so that it is capable of accommodating an adequate number of secondary channels. Generally, it is preferred that the included angle of the primary channel be greater than the included angle of the secondary channels so as to accommodate two or more secondary channels at the base of the primary channel. Generally, the secondary channels have an included angle at least 20 percent smaller than the included angle of the primary channel (for V-shaped primary channels).

With reference to FIGS. 1*d* and 1*i*, the depth, d, of the primary channels 102, 122, which is the height of the peaks or tops above the lowermost channel notch, is preferably substantially uniform. Depth, d, is suitably from about 5 to about 3000 microns, typically from about 50 to about 3000 microns, preferably from about 75 to about 1500 microns, and most preferably is from about 100 to about 1000 microns. It will be understood that in some embodiments, films with channels 102, 122 having depths, d, larger than the indicated ranges may be used. If the channels 102, 122 are unduly deep, the overall thickness of the fluid control film will be unnecessarily high and the film may tend to be stiffer than is desired.

Figure 11:
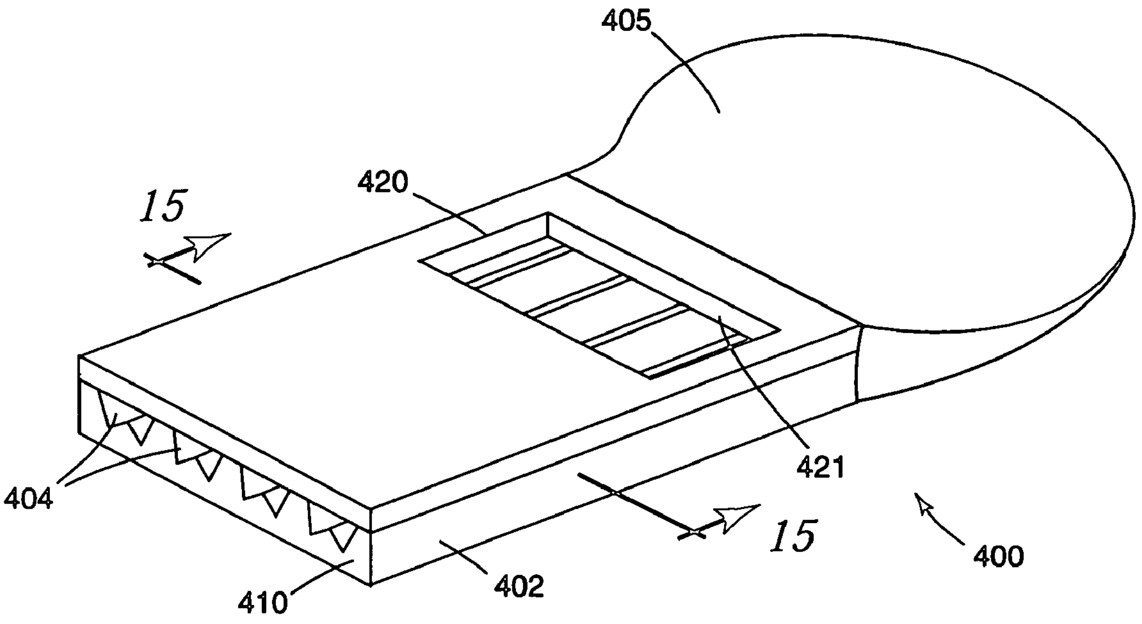
FIG. 11 is a perspective view of a detection article in accordance with the present invention including a fluid control film layer, a cap layer and a handle.

FIGS. 1*i* and 1*j* illustrate fluid control films 112*i* and 112*j* having primary channels on both major surfaces 120 and 121. As shown in FIG. 11, the primary channels 122 may be laterally offset from one surface 120 to the other surface 121, or may be aligned directly opposite each other as shown in FIG. 1*j*. A fluid control film 112*i* with offset channels as shown in FIG. 1*i* provides a maximum amount of surface area for fluid transport while at the same time using a minimum amount of material. In addition, a fluid control film 112*i* with offset channels can be made so as to feel softer, due to the reduced thickness and stiffness of the sheet, than a fluid control film 112*j* with aligned channels as shown in FIG. 1*j*. Referring to FIG. 1*j*, fluid control films 112*j* usable with the present invention may have one or more holes or apertures 124 therein, which enable a portion of the liquid in contact with the first surface 120 of the fluid control film 112*j* to be transported to the second surface 121 of the film to improve liquid control and increase versatility in liquid flow. The apertures 124 need not be aligned with a notch of a channel, but may be positioned wherever is necessary or convenient. In addition, the apertures 124 may vary in width from aperture to aperture, and may vary in width relative to the channels. The surfaces of the fluid control film within the apertures 124 are preferably designed to encourage fluid flow through the aperture 124.

As representatively illustrated in FIGS. 1*d* and 1*i*, in each primary channel 102, 122 are at least two secondary channels 103, 123 and at least two notches 105, 125, the notch 105, 125 or notches of each secondary channel 103, 123 is separated by a secondary peak 106, 126. Generally, each secondary channel 103, 123 will generally have only one notch 105, 125, but a secondary channel 103, 123 will have two notches 105, 125 if the secondary channel 103, 123 is rectangular. The secondary peak 106, 126 for V-channel shaped secondary channels 103, 123 is generally characterized by an included angle Beta (β) which is generally equal to $(\alpha^1+\alpha^2)/2$ where $\alpha^1$ and $\alpha^2$ are the included angles of the two adjacent V-channel shaped secondary channels 103, 123, assuming that the two sidewalls forming each secondary channel are symmetrical and not curved. Generally, the angle β would be from about 10° to about 120°, preferably from about 10° to about 90°, and most preferably from about 20° to about 60°. The secondary peak could also be flat (in which case the included angle would theoretically be 0°) or even curved, e.g., convex or concave, with no distinct top or included angle. Preferably, there are at least three secondary channels 103, 123 and/or at least three notches for each primary channel 102, 122, including any notches 108 or 109 associated with the end channels as shown in FIG. 1*d*.

The depth, d', of one of the secondary channels 103, 123, which is the height of the top of the secondary peaks 106 over the notches 105 as shown in FIG. 1*d*, is uniform over the length of the fluid control films and is typically at least 5 microns. The depth, d', of the secondary channels 103, 123 is generally 0.5 to 80 percent of the depth of the primary channels, preferably 5 to 50 percent. The spacing of the notches 105, 125 on either side of a peak 106, 126 is also preferably uniform over the length of the fluid control film 112*i*, 112*j*. Preferably the primary and/or secondary channel depth and width varies by less than 20 percent, preferably less than 10 percent for each channel over a given length of the fluid control film. Variation in the secondary channel depth and shape above this range has a substantial adverse impact on the rate and uniformity of liquid transport along the fluid control film. Generally the primary and secondary channels are continuous and undisturbed.

Figure 2D:
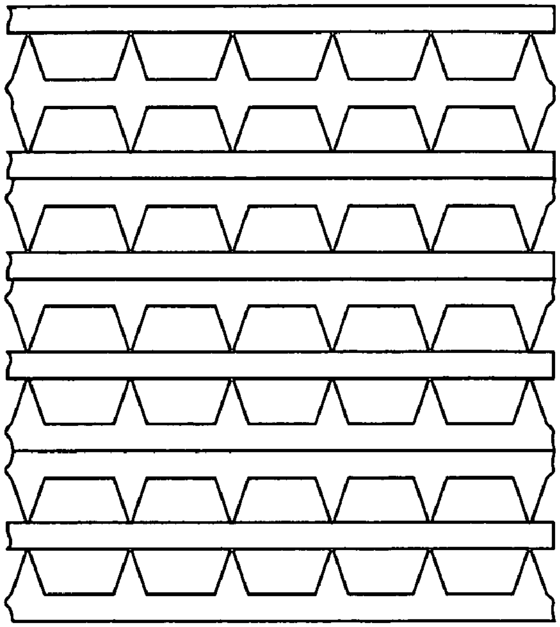
FIG. 2*d* is an end view of multiple stacked layers of fluid control film wherein microstructured channels form closed capillaries between layers and some layers have primary channels on both major surfaces.
Figure 2E:
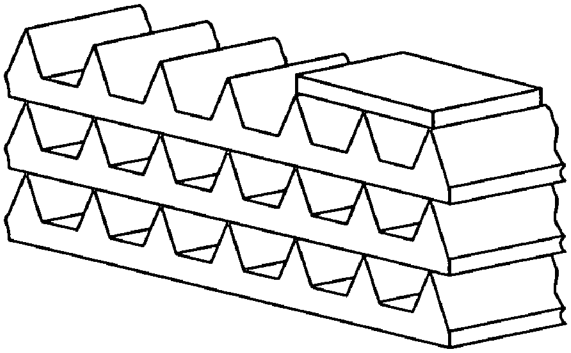
FIG. 2*e* is a perspective view of multiple stacked layers of fluid control film wherein an optional top cover film or cap is employed to enclose at least a portion of the channels of topmost layer.

Referring now to FIGS. 2*a*–2*f*, the fluid control film component usable with the present invention may also comprise multiple layers of microreplicated film or channels in various configurations, including but not limited to: simple stacks of the fluid control film or channels (see FIGS. 2*a*–2*c*), laminated layers of the fluid control film or channels forming closed capillaries between layers (see FIG. 2*d*), as well as stacks of layers having primary channels on both major surfaces (see FIG. 2*d*). The channels, or at least a portion of the channels, of a lower film may be enclosed by the bottom surface of an upper film. For example, as shown in FIG. 2*b*, in a stack 150 of structured layers 152, the bottom of a film layer 154 may enclose the channels 155 of an adjacent film layer 156. If desired, an optional top cover film or cap may be employed to enclose the channels of topmost film, as shown in FIG. 2*e*. In addition, one or more of the stacked layers, whether one microstructured surface or two such surfaces, may include one or more apertures, such as those shown in FIG. 1*j*, that provide fluid communication between layers of the stack. Optionally, a formed stack of microstructured layers may then be sliced, if desired, to form thin, multi-channel arrays.

Figure 2F:
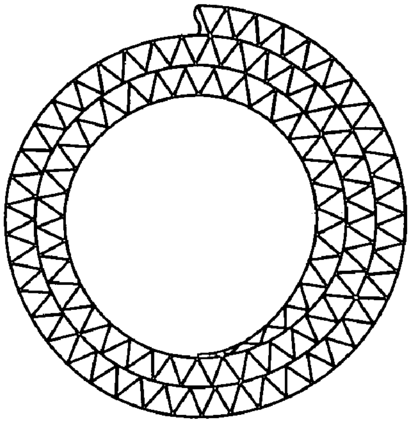
FIG. 2*f* is an end view of a single layer of fluid control film rolled to form a multi-layer spiral configuration.

Alternatively, as shown in FIG. 2*f*, the fluid control film usable with the present invention, may be formed as a single film layer wrapped in a roll fashion to create the enclose channels in a spiral configuration. If desired, a microreplicated film, which prior to wrapping has open channels on one surface, can be laminated with a double-sided adhesive layer and then rolled. The adhesive layer will bond adjacent layers of the roll together, thereby sealing the channels. Optionally, the rolled fluid control film may then be sliced into thin disks of channels that may be used as multiple array test modules.

The channels may have an included angle of between about 10 degrees and 120 degrees. Preferably, the channels are between about 5 and 3000 microns deep, with dimensions of between about 50 and 1000 microns deep being most preferred.

Certain of the fluid control films usable with the present invention are capable of spontaneously and uniformly transporting liquids (e.g., water, urine blood or other aqueous solutions) along the axis of the film channels. This capability is often referred to as wicking. Two general factors that influence the ability of fluid control films to spontaneously transport liquids are (i) the structure or topography of the surface (e.g., capillarity, shape of the channels) and (ii) the nature of the film surface (e.g., surface energy). To achieve the desired amount of fluid transport capability a designer may adjust the structure or topography of the fluid control film and/or adjust the surface energy of the fluid control film surface.

In order to achieve wicking for a fluid control film, the surface of the film must be capable of being "wet" by the liquid to be transported. Generally, the susceptibility of a solid surface to be wet by a liquid is characterized by the contact angle that the liquid makes with the solid surface after being deposited on a horizontally disposed surface and allowed to stabilize thereon. This angle is sometimes referred to as the "static equilibrium contact angle," and sometimes referred to herein merely as "contact angle."

Figure 3A:
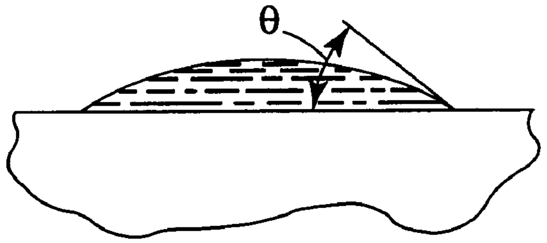
FIG. 3*a* is a partial side view of a droplet of liquid on a surface having a contact angle less than 90 degrees.
Figure 3B:
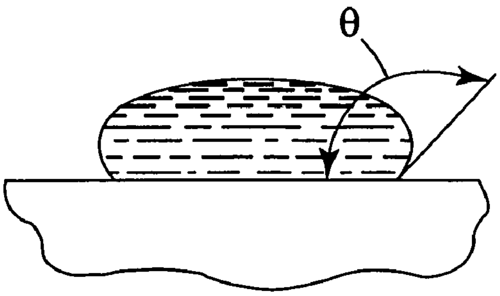
FIG. 3*b* is a partial side view of a droplet of liquid on a surface having a contact angle greater than 90 degrees.

Referring now to FIGS. 3*a* and 3*b*, the contact angle Theta, θ, is the angle between a line tangent to the surface of a bead of liquid on a surface at its point of contact to the surface and the plane of the surface. A bead of liquid whose tangent was perpendicular to the plane of the surface would have a contact angle of 90°. If the contact angle is greater than 90°, as shown in FIG. 3*b*, the solid surface is considered not to be wet by the liquid and is referred to as being inherently "hydrophobic." Hydrophobic films include polyolefins, such as polyethylene or polypropylene.

Typically, if the contact angle is 90° or less, as shown in FIG. 3*a*, the solid surface is considered to be wet by the liquid. Surfaces on which drops of water or aqueous solutions exhibit a contact angle of less than 90° are commonly referred to as "hydrophilic". As used herein, "hydrophilic" is used only to refer to the surface characteristics of a material, i.e., that it is wet by aqueous solutions, and does not express whether or not the material absorbs aqueous solutions. Accordingly, a material may be referred to as hydrophilic whether or not a sheet of the material is impermeable or permeable to aqueous solutions. Thus, hydrophilic films used in fluid control films of the invention may be formed from films prepared from resin materials that are inherently hydrophilic, such as for example, poly(vinyl alcohol). Liquids which yield a contact angle of near zero on a surface are considered to completely wet out the surface.

Depending on the nature of the microreplicated film material itself, and the nature of the fluid being transported, one may desire to adjust or modify the surface of the film in order to ensure sufficient capillary forces of the film. For example, the structure of the surface of the fluid control film may be modified to affect the surface energy of the film. The fluid control films of the invention may have a variety of topographies. As described above, preferred fluid control films are comprised of a plurality of channels with V-shaped or rectangular cross-sections, and combinations of these, as well as structures that have secondary channels, i.e., channels within channels. For open channels, the desired surface energy of the microstructured surface of V-channeled fluid control films is such that:

$$\text{Theta} \leqq (90° - \text{Alpha}/2),$$

wherein Theta (θ) is the contact angle of the liquid with the film and Alpha (α) is the average included angle of the secondary V-channel notches. (See, e.g., FIG. 1*g*).

It has been observed that secondary channels with narrower included angular widths generally provide greater vertical wicking distance. However, if Alpha is too narrow, the flow rate will become significantly lower. If Alpha is too wide, the secondary channel may fail to provide desired wicking action. As Alpha gets narrower, the contact angle Theta of the liquid need not be as low, to get similar liquid transport, as the contact angle Theta must be for channels with higher angular widths. Therefore, by modifying the geometry of the structured surface of the fluid control film, the surface energy and thus the wicking capability of the film may be modified to improve the liquid transport capability of the film.

Another example of modifying the surface of the film in order to ensure sufficient capillary forces of the film, is by modifying the surface in order to ensure it is sufficiently hydrophilic. Biological samples that will come into contact with the fluid control films of the present invention are aqueous. Thus, if such films are used as fluid control films of the invention, they generally must be modified, e.g., by surface treatment, application of surface coatings or agents, or incorporation of selected agents, such that the surface is rendered hydrophilic so as to exhibit a contact angle of 90° or less, thereby enhancing the wetting and liquid transport properties of the fluid control film. Methods of making the surface hydrophilic include: (i) incorporation of a surfactant; (ii) incorporation or surface coating with a hydrophilic polymer; (iii) treatment with a hydrophilic silane; and (iv) treatment with an inorganic thin film coating such as $SiO_2$, which becomes hydrophilic upon exposure to moisture. Other methods are also envisioned.

Any suitable known method may be utilized to achieve a hydrophilic surface on fluid control films used with the present invention. Surface treatments may be employed such as topical application of a surfactant, plasma treatment, vacuum deposition, polymerization of hydrophilic monomers, grafting hydrophilic moieties onto the film surface, corona or flame treatment, etc. An illustrative method for surface modification of the films of the present invention is the topical application of a one percent aqueous solution of a material comprising 90 weight percent or more of:

Formula 1

$$C_nF_{2n+1}SO_2N(CH_2CH_3)(CH_2CH_2O)_{7.5}CH_3$$

wherein n=8 (97 percent), n=7 (3 percent), and 10 weight percent or less of:

Formula 2

$$C_nF_{2n+1}SO_2N(CH_2CH_3)H$$

wherein n=8 (97 percent), n=7 (3 percent). Preparation of such agents is disclosed in U.S. Pat. No. 2,915,554 (Ahlbrecht et al.).

Alternatively, a surfactant or other suitable agent may be blended with the resin as an internal additive at the time of film extrusion. It is typically preferred to incorporate a surfactant in the polymeric composition from which the fluid control film is made rather than rely upon topical application of a surfactant coating because topically applied coatings tend to fill in, i.e., blunt, the notches of the channels, thereby interfering with the desired liquid flow to which the invention is directed. An illustrative example of a surfactant that can be incorporated in polyethylene fluid control films is TRITON™ X-100, an octylphenoxypolyethoxyethanol nonionic surfactant, e.g., used at between about 0.1 and 0.5 weight percent.

Preferred embodiments of the present invention retain the desired fluid transport properties throughout the life of the product into which the fluid control film is incorporated. In order to ensure the surfactant is available throughout the life of the fluid control film the surfactant preferably is available in sufficient quantity in the article throughout the life of the article or is immobilized at the surface of the fluid control film. For example, a hydroxyl functional surfactant can be immobilized to a fluid control film by functionalizing the surfactant with a di- or tri-alkoxy silane functional group. The surfactant could then be applied to the surface of the fluid control film or impregnated into the article with the article subsequently exposed to moisture. The moisture would result in hydrolysis and subsequent condensation to a polysiloxane. Hydroxy functional surfactants (especially 1,2 diol surfactants) may also be immobilized by association with borate ion. Suitable surfactants include anionic, cationic, and non-ionic surfactants, however, nonionic surfactants may be preferred due to their relatively low irritation potential. Polyethoxylated and polyglucoside surfactants are particularly preferred including polyethoxylated alkyl, aralkyl, and alkenyl alcohols, ethylene oxide and propylene oxide copolymers such as "Pluronic" and "Tetronic", alkylpolyglucosides, polyglyceryl esters, and the like. Other suitable surfactants are disclosed in Ser. No. 08/576,255, which is herein incorporated by reference. Alternatively, a hydrophilic monomer may be added to the article and polymerized in situ to form an interpenetrating polymer network. For example, a hydrophilic acrylate and initiator could be added and polymerized by heat or actinic radiation.

Suitable hydrophilic polymers include: homo and copolymers of ethylene oxide; hydrophilic polymers incorporating vinyl unsaturated monomers such as vinylpyrrolidone, carboxylic acid, sulfonic acid, or phosphonic acid functional acrylates such as acrylic acid, hydroxy functional acrylates such as hydroxyethylacrylate, vinyl acetate and its hydrolyzed derivatives (e.g. polyvinylalcohol), acrylamides, polyethoxylated acrylates, and the like; hydrophilic modified celluloses, as well as polysaccharides such as starch and modified starches, dextran, and the like.

As discussed above, a hydrophilic silane or mixture of silanes may be applied to the surface of the fluid control film or impregnated into the article in order to adjust the properties of the fluid control film or article. Suitable silane include the anionic silanes, disclosed in U.S. Pat. No. 5,585,186 which is herein incorporated by reference, as well as non-ionic or cationic hydrophilic silanes. Cationic silanes may be preferred in certain situations and have the advantage that certain of these silanes are also believed to have antimicrobial properties.

As also described above, thin film inorganic coatings, such as $SiO_2$, may be selectively deposited on portions of the fluid control film or impregnated into the article, e.g., on the interior surface of microchannels. Deposition may occur either in-line during manufacture of the fluid control film or in a subsequent operation. Examples of suitable deposition techniques include vacuum sputtering, electron beam deposition, solution deposition, and chemical vapor deposition. $SiO_2$ coating of the fluid control film may provide the added benefit of producing a more transparent film than other types of coatings or additives. In addition, an $SiO_2$ coating does not tend to wash off over time the way other coatings or additives may.

The inorganic coatings may perform a variety of functions. For example, the coatings may be used to increase the hydrophilicity of the fluid control film or to improve high temperature properties. Application of certain coatings may facilitate wicking a sizing gel, filtration gel or assay reagent gel into the microchannels, for example. Conductive coatings may be used to form electrodes or diaphragms for piezoelectric or peristaltic pumping. Coatings may also be used as barrier films to prevent outgassing.

An article, such as a wick, may be formed from a fluid control film having the capability of spontaneous fluid transport, as described above, and may be configured with either open or closed channels. In order for a closed channel wick made from a fluid control film to function, the wick is preferably sufficiently hydrophilic to allow the desired fluid to wet the surface of the fluid control film. In order for an open channel wick to function, the fluid must not only wet the surface of the fluid control film, but also the surface energy of the film must be at an appropriate level, such that the contact angle Theta between the fluid and the surface is equal or less than 90 degrees minus one-half the notch angle Alpha, as set forth above.

Detection Articles

Figure 4:
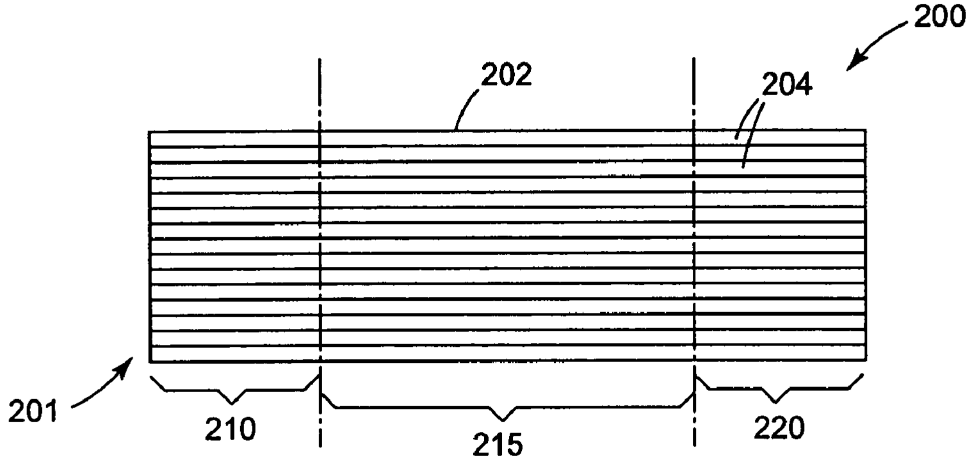
FIG. 4 is a top view of a detection article in accordance with the present invention having a plurality of open parallel microstructured channels including an acquisition zone and a detection zone.

Referring now to FIG. 4, a miniaturized detection device of the present invention, referred to herein as a detection article 200, is formed from at least one layer 202 of a fluid control film, as described above, that includes a plurality of coextensive channels 204 preferably extending uninterrupted along the length of the article. As used herein, the term "coextensive" describes a continuous flow path through a channel. Along the length of the channels 204, the detection article 200 includes an acquisition zone 210 and a detection zone 220. The channels 204 provide a means to wick or transport a liquid sample into the acquisition zone 210, between the acquisition zone 210 and the detection zone 220, and into the detection zone 220, by spontaneous and uniform fluid transport, or capillary action, throughout the length of the channels 204. Although shown as separate and non-overlapping areas of the article 200, it is to be understood that the acquisition zone 210 and the detection zone 220 may overlap partially or completely, if desired.

The detection article 200 is designed to acquire a fluid sample at the acquisition zone 210, which then may be tested in some manner to cause a detectable characteristic at the detection zone 220. The fluid sample to be tested may be derived from a source such as, but not limited to, a physiological fluid including blood, serum, plasma, saliva, ocular lens fluid, cerebral spinal fluid, pus, sweat, exudate, urine, milk or the like, or from a source such as a food or beverage sample, a sterilization assay reagent, or a biological research sample. The sample may be subjected to prior treatment such as, but not limited to, extraction, addition, separation, dilution, concentration, filtration, distillation, dialysis or the like. Besides physiological fluids, other liquid test samples may be employed and the components of interest may be either liquids or solids whereby the solids are dissolved or suspended in a liquid medium. These other samples may be related to such areas as sterilization monitoring, food microbiology, water testing and drug testing. Detection articles of the present invention are generally useful in detecting biological materials usable in biomedical R&D, pharmaceutical drug discovery, medical diagnostics, food and agricultural microbiology, military and forensic analysis.

As described above, the fluid control layer, such as layer 200, may be formed as an integral part of the article 200. Alternatively, the fluid control film structure (e.g., its microreplicated pattern of channels 204) may be incorporated into the detection article 200 as a separable component, wherein the article further includes a support component that may or may not be attached to a cover layer allowing for replacement of the fluid control layer. Optionally, the fluid control film layer 202 may be removably incorporated into a detection device, such as those described below for detecting a characteristic within the fluid sample at the detection zone, and may be changed out and replaced for each subsequent test. It should be understood that the microreplicated pattern or layer may be made off-line of the detection article 200 or may be made integral with a converting operation for the detection article 200.

Figure 5:
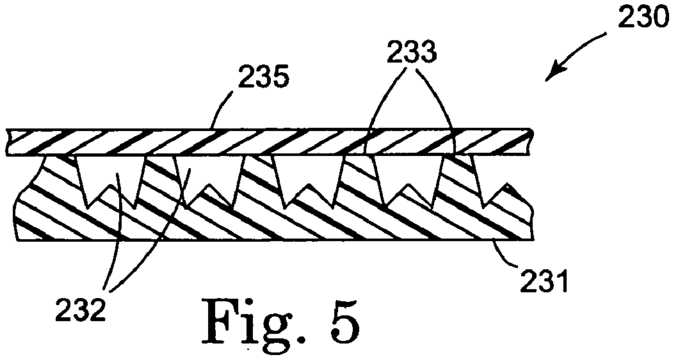
FIG. 5 is a partial cross-sectional view of a detection article in accordance with the present invention have a plurality of microstructured channels at least partially enclosed by a cap layer.

The detection article 200 may be formed with open channels 204. Optionally, as shown in FIG. 5, a detection article 230 may be formed with closed channels 232, wherein a cover or cap layer 235 is positioned and possibly sealed over some or all of the channels 232 and/or over the entire length of the channels 232 or just a portion of the length of the channels 232. Suitable cap layers will be described in more detail below.

The acquisition zone 210 serves as an interface between the liquid sample and the detection article 200. The acquisition zone 210 preferably provides a sufficient acquisition surface to introduce a desired volume of sample into the microstructure of the article 200. Towards this end, the acquisition zone 210 preferably includes two or more channels 204 that are capable of wicking a fluid sample into the article 200 by spontaneous liquid transport, as described above. Therefore, the channels 204 must be suitably hydrophilic such that they are capable of being wet by the liquid sample to be tested. If the channels 204 are open, the channels 204 must additionally be provided with an appropriate surface energy level to achieve a wicking action and introduce the sample into the channels 204, as set forth above. Also, using a plurality of channels 204, fluid movement is ensured in the event that a single channel becomes blocked or fails to wick fluid to the detection zone 220. Although the acquisition zones of the present invention are capable of wicking a fluid sample into the detection article unaided, it is to be understood that other fluid transport methods may additionally be provided, such as pressure differential, electrophoresis or pumping, if desired.

Figure 6A:
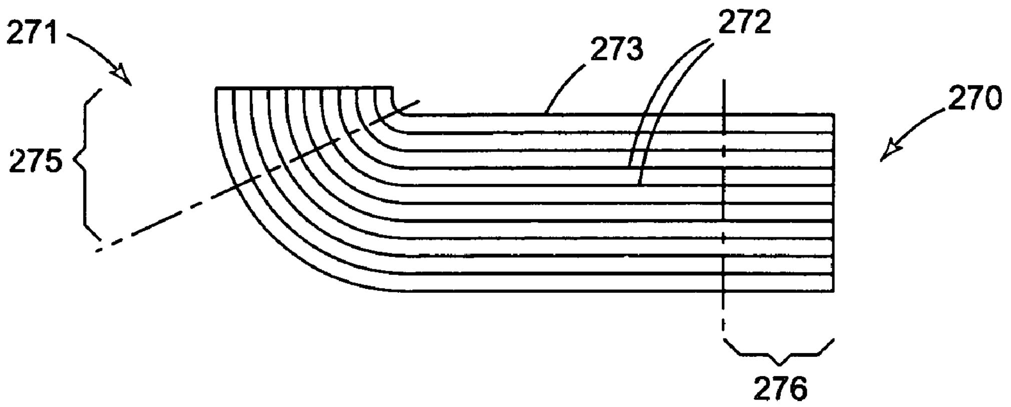
FIG. 6*a* is a top view of a detection article in accordance with the present invention having a plurality of open parallel microstructured channels that bend 90 degrees at the acquisition zone end.

One example of an acquisition zone 210 in accordance with the present invention is shown in FIG. 4. In this embodiment, the channels 204 are open on one end 201 of the article 200, such that the channels 204 may be placed in fluid contact with the liquid sample resulting in transport of the sample into the channels 204 by the wicking action of the article 200. Referring now to FIG. 6*a*, another embodiment of a detection article 270 is shown formed from a fluid control film layer 273 having a plurality of microstructured channels 272. The channels 272 include a bend at one end 271 of the article 270, such that the direction of the channels 272 changes by 90 degrees. As a result, an acquisition zone 275 includes a plurality of channel openings that open along the length of the article 270, instead across the width as in article 200. A detection zone 276 is provided at the opposite end of the article 270. In a similar manner, the channels of a detection article may be oriented and/or reoriented in any direction as is needed to meet the requirements of the article.

Figure 6B:
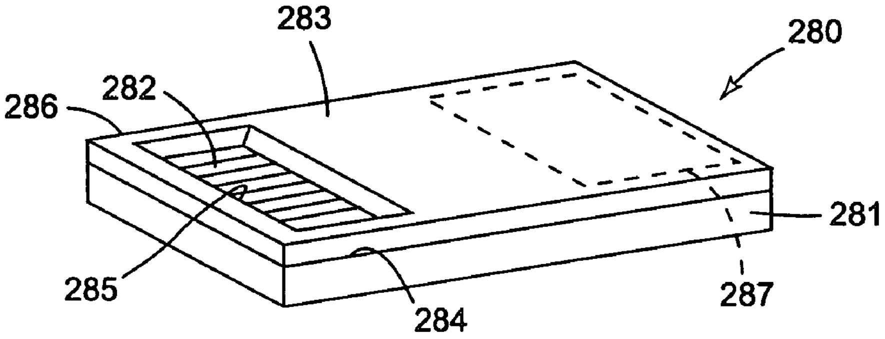
FIG. 6*b* is a perspective view of a detection article in accordance with the present invention including a microstructured fluid control film layer and cap layer having an aperture at the acquisition zone.

Referring now to FIG. 6*b*, yet another embodiment of a detection article 280 is shown formed from a fluid control film layer 281 having a plurality of microstructured channels 282. A cap layer 283 is also provided, which covers the channels 282. In this embodiment, the channels 282 are not open at the ends, either across the width or along the length, but instead are exposed on the top surface 284 through an aperture 285 formed within the cap layer 283, which in turn forms an acquisition zone 286. The fluid sample may be introduced at the aperture 285 and allowed to wick into the plurality of channels 282 and thus flow through the article 280 into a detection zone 287, also provided at the opposite end of the article 280.

Figure 6C:
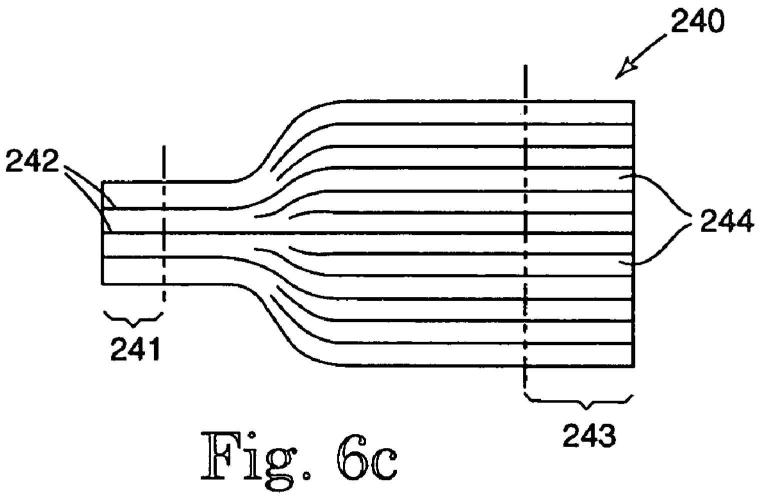
FIG. 6*c* is a top view of a detection article in accordance with the present invention including an acquisition zone and a detection zone each having a different number of microstructured channels than the other.

As shown in FIG. 6*c*, channels 242 in an acquisition zone 241 may differ in number than channels 244 in a detection zone 243 of a particular detection article 240. Although shown with less channels 242 in the acquisition zone 241 than channels 244 in the detection zone 243, the article 240 may be configured so that the opposite is true—more acquisition channels 242 than detection channels 244. However, in either case, flow of the sample liquid from the acquisition zone 241 to the detection zone 243 remains continuous and uninterrupted.

Figure 7:
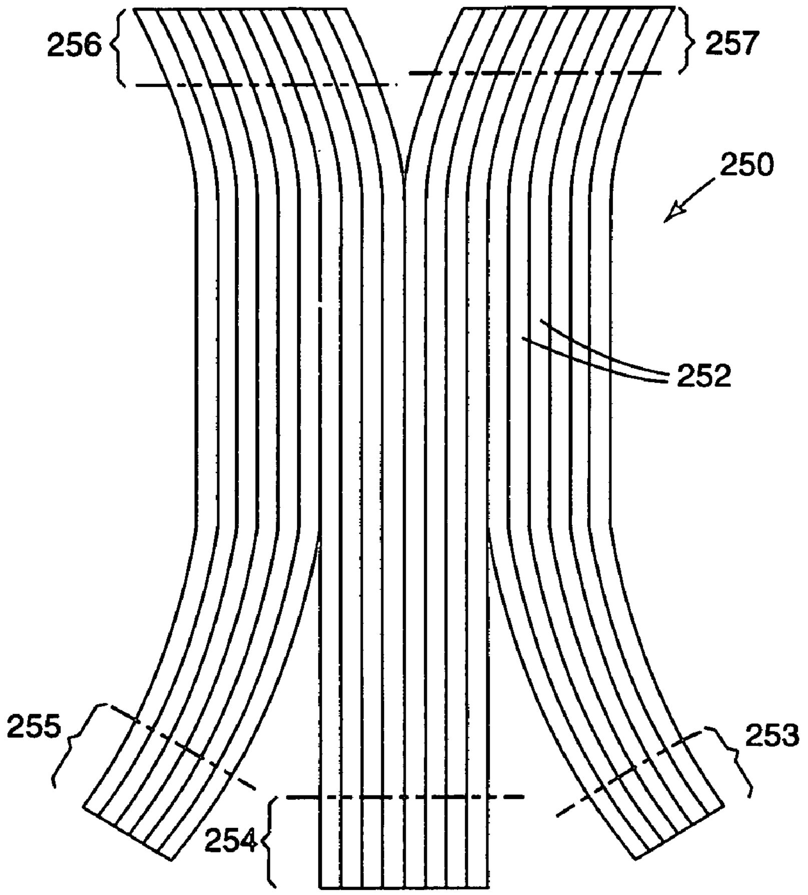
FIG. 7 is a top view of a detection article in accordance with the present invention including multiple separated acquisition zones and multiple separated detection zones.

Referring representatively to FIG. 4, the channels 204 may be coextensively adjacent within the acquisition zone 210. As shown in FIG. 7, however, the channels 252 of detection article 250 may be split apart into two or more separate multiple channel acquisition zones, such as 253, 254 and 255, if desired in order to introduce more than one liquid sample into the detection article 250. Due to the extremely thin nature of the fluid control film layers provided in the present invention, the acquisition zone of a detection article may possibly be split apart into two or more separated acquisition zones as needed by a user at the time of a test, if desired. Optionally, perforations or other aids for channel splitting may be provided to facilitate separation into multiple acquisition zones if and when needed. Separate acquisition zones 253, 254, 255 may remain separated throughout the detection article 250, thus flowing into separate and corresponding detection zones (not specifically shown). Alternately, the separate acquisition zones 253, 254, 255 may converge together to allow flow into a common detection zone (not shown), or may converge together and then split apart again into different detection zones 256, 257 (as described more below).

The channels 204 are continuous from the acquisition zone 210 through the detection zone 220 providing continuity of sample flow throughout the detection article 200. Although shown in the illustrative embodiments as including parallel channels, it is to be understood that detection articles of the present invention may also comprise other channel configurations, including but not limited to converging, diverging, and/or intersecting channels, as long as uninterrupted fluid flow between the acquisition zone and detection zone is maintained. In preferred embodiments, sample flow within the channels 204 is also discrete, in that the liquid sample enters each individual channel and the sample within a specific channel remains in that channel from the acquisition zone 210 through the detection zone 220. That is, transport of sample across channels does not generally occur. A cap layer, such as cap layer 235, sealed to the fluid control layer 202 may facilitate the discreteness of the channels 204 by enclosing each channel and sealing each channel from adjacent channels 204. However, open channels 204 will also remain substantially discrete due to surface tension of the liquid within the channels 204. In addition, for detection articles formed from a plurality of layers, such as those shown in FIGS. 2*a*–2*f* which will be described in more detail below, or for layers with multiple microstructured surfaces, such as those shown in FIGS. 1*i*–*j*, apertures may be provided which allow for fluid communication between layers or between surfaces of a layer.

The continuous flow capability of the detection articles of the present invention differs from other, more traditional, detection articles that include an inlet port to which a liquid sample is introduced or presented and from which the sample flows to other areas of the article. In these more traditional articles, sample handling and input mechanisms, such as syringes, are employed to insert liquid into the article through the input port, which is often an aperture opening into a void or containment area from which the liquid sample flows into the remainder of the article. Alternatively, a sample handling and input mechanism may insert or deliver sample directly into individual channels. In the present invention, however, no such sample handling or input mechanisms are required, only fluid contact between the acquisition zone 210 and a liquid sample is necessary. The present invention thus simplifies the detection process, as well as reduces labor, time, materials and, therefore, costs.

In some embodiments, the detection zone 220 is immediately adjacent the acquisition zone 210, or there may be an overlap of the detection zone 220 and the acquisition zone 210. In other embodiments, separation of the acquisition and detection zones 210, 220 may be desired, such that a transitional or intermediate zone 215 of channels 204 is provided. The intermediate zone 215 may be provided for functional purposes, such as time delay, wherein a sample analysis to be detected requires a time period during which a reaction or other process occurs and flow along an added length of channel provides the desired time delay before reaching the detection zone 220. In addition, the intermediate zone 215 may provide an area for sample preparation prior to detection, including introduction of required compounds into the sample, sample exposure to one or more compositions for filtering or other purposes, and/or sample flow around or through a structure placed within the channel to cause turbulence or other sample mixing. Optionally, a portion of the detection zone 220 may also or instead be used for sample preparation prior to detection. Alternatively, the intermediate zone 215 may be provided for structural purposes, such as strengthening of the article 200, increase in size of the article 200 for easier handling, or other appropriate reasons. It is to be understood, however, that the intermediate zone 215, if provided, may serve both functional and structural purposes.

Referring again to FIG. 4, the detection zone 220 preferably includes one or more of the channels 204 that provide continuous and uninterrupted fluid flow for the liquid sample acquired into the detection article 200 at the acquisition zone 210. In a manner similar to the multiple acquisition zones 253, 254, 255 described above and shown in FIG. 7, the detection article 250 may also include a plurality of detection zones, such as 256 and 257, which allow for one or more test samples to be analyzed and detected separately. Optionally, the detection article 250 may include multiple detection zones 256, 257 and only a single acquisition zone (similar to zone 210 shown in FIG. 4). It is also possible that a single detection zone may be split apart by the user at the time of the test, if desired, to provide multiple detection zones.

The detection zone 220 provides for the detection of a characteristic of the fluid sample within the detection zone 220, including but not limited to a result of an event, such as a chemical or biological reaction, or a condition, such as temperature, pH or electrical conductivity, within one or more of the channels 204. The detection zone 220 includes at least one detection element (not shown), which is any composition of matter or structural member that facilitates detection of the characteristic. Facilitation of detection is meant to encompass any involvement in the detection process and/or any modification of the fluid sample for the purposes of enabling detection. The detection element may include, but is not limited to hardware devices, such as a microoptical, microelectronic or micromechanical devices, assay reagents, and/or sample purification materials. The detection element is preferably positioned in fluid contact with the liquid sample transported to the detection zone 220, such as within the channels 204 in a manner consistent with the type of detection element provided. However, the detection element may instead be positioned adjacent the channels 204, such as in cap layer 235 Shown in FIG. 5, or in another suitable location, either in fluid contact or not in fluid contact with the fluid sample. Optionally, one or more detection elements may be positioned within channels 204 with one or more other detection elements located in the cap layer 235, or other location as desired. Alternatively, one or more detection elements may be positioned within channels 204 and/or in the cap layer 235 with one or more other detection elements located external to the detection article 200. Additional detection elements may also be provided within the channels 204 outside of the detection zone, if desired, in order to aid in sample preparation for detection, such as, for example, a sample purification material provided prior to the detection zone 220 containing an assay reagent.

A single detection element may be used to facilitate detection of characteristics from the fluid sample in one or more channels 204. Alternatively, multiple elements may be used to facilitate detection of characteristics from the fluid sample in one or more channels 204. The multiple detection elements may be all of one type, or may be of different types that are capable of facilitating detection of different characteristics from the liquid sample or samples provided. In one embodiment, a different detection element may be positioned within each separate channel 204 within the detection zone 220 of the article 200, facilitating detection of different characteristics within each channel 204. Alternatively, the same type of detection element, but at different concentrations or quantities, may be positioned within each separate channel 204 facilitating detection of varying levels of characteristics within each channel 204. Such different detection elements may be offset from channel to channel within the detection zone 220 so as to increase the ease of detection within adjacent channels 204. In embodiments having multiple detection zones, such as 256 and 257 in FIG. 7, one or more detection elements may be provided in each zone 256, 257 that facilitate detection of the same, different, or different levels of characteristics within each zone 256, 257.

As set forth above, the detection elements may include hardware devices, such as but not limited to one or more microelectronic, microoptical, and/or micromechanical devices. Examples of microelectronic elements include conductive traces, electrodes, electrode pads, microheating elements, electrostatically driven pumps and valves, microelectromechanical systems (MEMS), and the like. The microelectrical elements may also include for example flexible microinterconnect circuitry to support electrochemical or conductivity based detection or to support optical elements requiring external power. Examples of microoptical elements include optical waveguides, waveguide detectors, reflective elements (e.g., prisms), beam splitters, lens elements, solid state light sources and detectors, and the like. The microoptical elements may also include for example microreplicated optical elements such as microlenses, wavelength selective gratings, and transmission enhancing microstructures. Examples of micromechanical elements include filters, valves, pumps, pneumatic and hydraulic routing, and the like. These hardware devices may be incorporated in the cover layer, either surface of the fluid control film, an additional polymeric substrate bonded to the fluid control film, or a combination thereof.

The hardware devices serve a variety of functions. For example, microelectronic devices that make contact with the fluid sample at particular points in the detection zone can be designed to measure a change in conductivity or a change in concentration of an electrochemical agent in response to the amount of analyte present in the sample. Microelectronic devices that contact the fluid may also be designed to concentrate the sample in a portion of the detection zone by free field electrophoresis based on the charge of the biological analyte alone or in combination with other assay reagents.

It is also possible to design hardware devices that do not contact the fluid. For example, microelectronic devices can be designed to lie in close proximity to the channels of the detection article such that they can be used to heat and cool fluid samples within the channels, or to establish different temperatures within the detection article. For example, elevated temperatures may be used to speed the amplification of a DNA fragment of interest or to speed the growth of a growing microbial colony of interest. In addition, microelectronic devices lying in close proximity to the channels of the detection zone may be designed to form an antenna to detect AC impedance changes useful for detecting analytes in a microfluidic separation system.

There are several different ways to incorporate microelectronic, microoptical, and/or micromechanical devices into the fluid control film layer or the detection articles of this invention. For example, the devices may be incorporated into the cover film layer, as mentioned above and described in detail co-owned and co-pending application Ser. No. 09/099,562. Another method for incorporating hardware devices into the article involves providing a flexible polymeric substrate bearing a series of electrically conductive traces (e.g., traces made from nickel, gold, platinum, palladium, copper, conductive silver-filled inks, or conductive carbon-filled inks), and then forming the microstructured surface on a surface of this substrate. Examples of suitable substrates include those described in Klun et al., U.S. Pat. No. 5,227,008 and Gerber et al., U.S. Pat. No. 5,601,678. The substrate then becomes the fluid control film layer.

The microstructured surface including the microelectronic devices may be formed in several ways. For example, the conductive trace-bearing surface of the substrate may be brought into contact with a molding tool having a molding surface bearing a pattern of the microstructured fluid control pattern. Following contact, the substrate is embossed to form the microstructured surface on the same surface as the conductive traces. The trace pattern and molding surface are designed such that the conductive traces mate with appropriate features of the fluid control pattern.

It is also possible, using the same molding tool, to emboss the microstructured surface onto the surface of the substrate opposite the conductive trace-bearing surface. In this case, the non-trace bearing surface is provided with a series of electrically conductive vias or through holes prior to embossing to link the conductive traces with appropriate structures of the microstructured surface.

Alternatively, it is possible to bond a separate polymeric substrate bearing microelectronic, microoptical, and/or micromechanical devices to the microstructured surface of a polymeric substrate using, e.g., a patterned adhesive such that the conductive traces mate with appropriate features of the microstructured surface.

It is also possible to introduce microelectronic, microoptical, and/or micromechanical devices into a separate polymeric substrate that is bonded to the fluid control film layer. To accomplish this objective, a flexible substrate having a series of electrically conductive vias and bumps on one of its major surfaces is used as a substrate. The microstructured surface is then molded as described above on the via and bump-bearing surface of the substrate.

It is also possible to introduce microelectronic, microoptical, and/or micromechanical devices into a separate polymeric substrate that is laminated to the fluid control film layer subsequent to molding. Yet another method for equipping the article with microelectronic, microoptical, and/or micromechanical devices involves taking a polymeric substrate having microstructured surface on one surface, and depositing a pattern of electrically conductive metal traces directly onto this surface using conventional metal deposition and photolithographic techniques.

As set forth above, the detection elements may include assay reagents and sample purification materials. The assay reagents may include for example, fluorogenic or chromogenic indicators, electrochemical reagents, agglutination reagents, analyte specific binding agents, amplification agents such as enzymes and catalysts, photochromic agents, dielectric compositions, analyte specific reporters such as enzyme-linked antibody probes, DNA probes, RNA probes, fluorescent or phosphorescent beads. The sample purification materials may include for example, filtration elements, chromatographic or electrophoretic elements, analyte specific binding agents (e.g. antibodies, antibody fragments, DNA probes) and solid supports for same. Numerous possible assay reagents and purification materials are set forth below in the discussion of various applications of the detection articles of the present invention and the Examples. It is possible to selectively deposit assay reagents, biological probes, biocompatible coatings, purification gels and the like onto various portions of the fluid control film. Alternatively, these materials may be deposited in a pre-determined pattern on the surface of the cap layer designed to contact the fluid control film.

The detection elements described above allow for detection by various methods known in the art. These methods may include color changes, fluorescence, luminescence, turbidity, electrical conductivity or voltage changes, light absorption, light transmission, pH, change in physical phase or the like. Detection of the characteristics by these methods may be provided manually, such as by visual observation or connection to an appropriate probe, or may be provided automatically using one or more types of detection mechanisms including, for example, a microplate reader for the detection of luminescence emission. Other detection methods are set forth below in the discussion of various applications of the detection articles of the present invention and the Examples.

The stacked fluid control film layers, described above and shown in FIGS. 2*a*–2*f*, may be used as a multi-parameter detection article, wherein the individual channels of the stacked array may contain unique detection elements. In this manner, individual channels may provide a positive response (such as, for example, a color change) while other channels do not, both within a single layer and from layer to layer. As with a single layer article, such detection elements and/or assay reagents may be offset, from channel to channel and/or from layer to layer, to facilitate ease of detection between adjacent channels and layers. This design provides a means to engineer (three dimensionally) the fluid flowpath, such that sample may flow through the channels on one layer and may optionally be allowed to flow between layers (such as by apertures provided within a layer as described above) during the course of flow through the detection article.

As stated above, the detection article, such as article 200 shown in FIG. 4, may be formed with open channels 204, or the detection article, such as article 230 shown in FIG. 5, may include an optional cover film or cap layer 235 that forms closed channels 232. The cap layer 235 may be secured to the other layer 231 by methods known in the art including, but not limited, to adhesion, welding or mechanical fastening. The cap layer 235 may be sealed to the peaks 233 of the individual channels 232 or may sealed only around the perimeter of the article 230. The cap layer 235 may be formed from a flat, relatively planar film, sheet, or other suitable layer, as shown.

Figure 8:
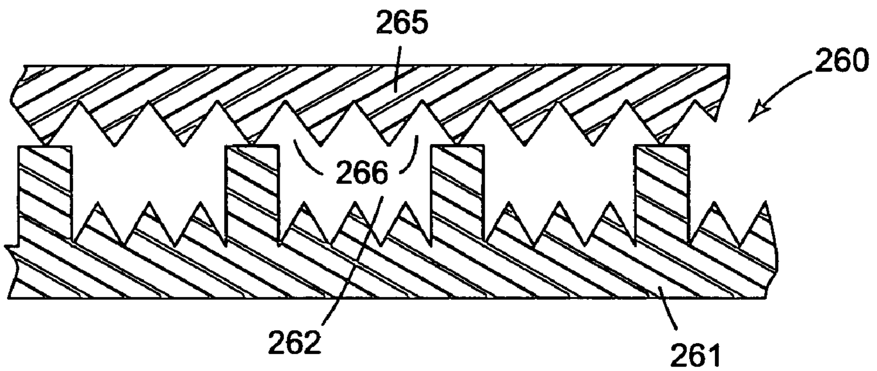
FIG. 8 is a partial cross-sectional view of a detection article in accordance with the present invention including a microstructured fluid control film cap layer.

Referring now to FIG. 8, a cap layer 265 of a detection article 260 may optionally be a microstructured fluid control film, such that the cap layer 265 includes a plurality of channels 266 formed in a manner similar to channels 262 of fluid control film layer 261. Optionally, the microstructured cap layer 265 may also be formed as a hydrophilic fluid control film having the properties set forth above, such that the cap layer 265 is also capable of spontaneous and uniform transport of liquids. The channels 266 may be of the same type or structure as channels 262, or may have a different structure, as shown.

Referring now to both FIGS. 5 and 8, the cap layer 235, 265 may cover all or only a portion of the channels 232, 262. Partial coverage may be provided by partially covering all of the channels 232, 262, fully covering some but not all of the channels 232, 262, or partially covering some of the channels 232, 262. Channel coverage, whether full or partial, may be desired for various reasons. In some embodiments, the cap layer 235, 265 may serve primarily as a protective layer over the channels 232, 262 or may serve to enclose the channels to provide discrete flow or to enhance the wicking action at the acquisition zone. Alternatively, the cap layer 265 may be a fluid control film that serves a fluid flow function, such that the cap layer 265 may be a detection article in its own right, or the cap layer 265 serves to enhance the wicking action at the acquisition zone. In yet other embodiments, the cap layer 235, 265 may function as part of the detection zone, such as by including one or more detection elements that are in fluid contact with the sample in channels 232, 262, as described above.

In addition, the cap layer 235, 265 may provide for a viewing region in the detection zone from which test characteristics may be observed and/or detected.

This viewing region may be an uncovered region due to partial coverage of the channels 232, 262, or may be a window at a desired located. The window may be open, such that the cap layer 235, 265 includes an aperture exposing the channels 232, 262. Alternatively, the window may be closed, such that the cap layer 235, 265 covers the channels 232, 262, but may be provided with a transparent region positioned in the detection zone, as desired. The transparent region may be provided by inclusion of a portion of transparent film inset in the cap layer 235, 265 at the desired location, or the transparent region may be provided by use of a transparent cap layer 235, 265.

Figure 9:
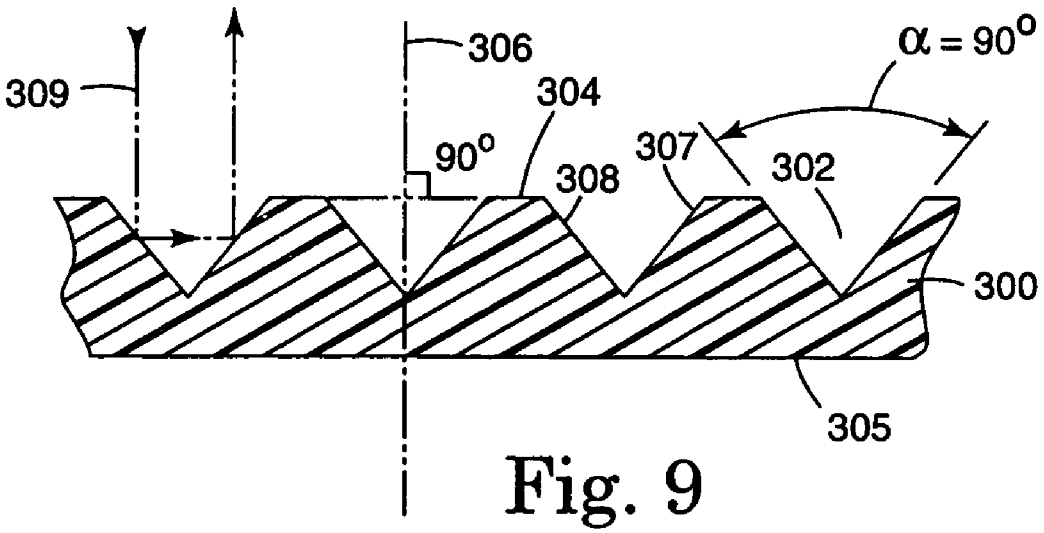
FIG. 9 is a partial cross-sectional view of a detection article in accordance with the present invention having V-shaped channels oriented normal to the microstructured surface.

In embodiments having a microstructured cap layer 265, the transparency of the cap layer 265 may be diminished or otherwise affected by the microstructured surface of the fluid control film. This reduction in transparency may be the result of channel angle affecting the retroreflection of the film and causing a loss of optical transmission. Referring now to FIG. 9, for a fluid control film layer 300 having a V-shaped channels 302 with 90 degree included angles, Alpha, that are oriented with the angle centers 306 normal (i.e., at 90 degrees) to the film layer's major surface 304, the angle of incident light becomes a significant factor in transparency of the film layer. For certain angles of incidence, a phenomenon known as total internal reflection (or TIR) will take place, resulting in a loss of optical transmission through the film layer. TIR generally occurs at an interface between a denser medium, such as the film layer, and a less dense medium, such as air, based on a relationship between the indices of refraction of the two mediums and the angle of incidence. The least angle of incidence at which TIR takes place is known as the critical angle. For film layers having microstructured surfaces, such as layer 300, TIR produces a situation wherein incident light (shown by phantom arrow 309) striking a first face or sidewall 307 of a channel 302 will undergo TIR and travel to the other sidewall 308 of the channel 302 and again undergo TIR causing the light to exit the sidewall 308 back in the direction from whence it came. As a result, no light will exit the film layer 300 through the opposite surface 305 and thus no viewable light will be transmitted through the film layer 300.

There are several methods for circumventing this optical problem. The first is to make the included angles of the channels flatter (i.e., greater than 90 degrees) so that TIR will not occur on both channel sidewalls. However, there is a limit to how flat the channel angles can be before the wicking capability of the channels is affected. It has been found that in order to optimize the wicking of a fluid control film layer, the included angle of the channels is preferably less than 90 degrees. A compromise angle of about 100 degrees has been found to allow for both wicking and light transmission, although neither function is optimized.

Figure 10A:
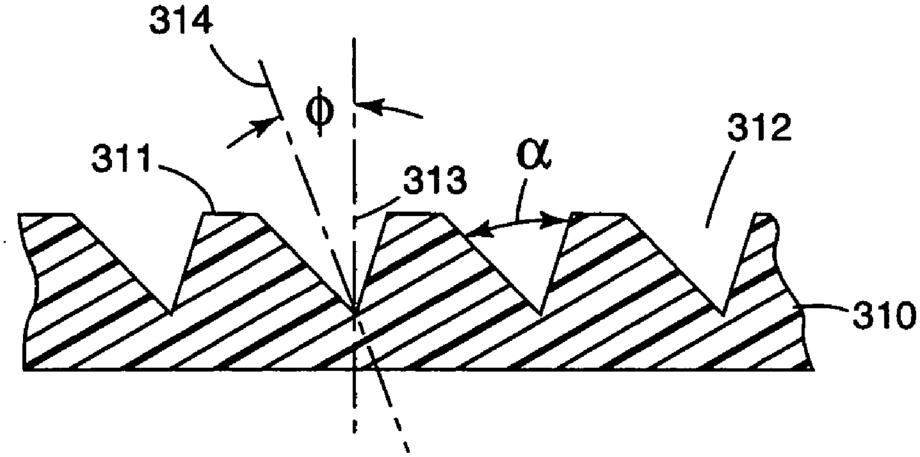
FIG. 10*a* is a partial cross-sectional view of a detection article in accordance with the present invention having V-shaped channels canted at an angle to the normal.
Figure 10B:
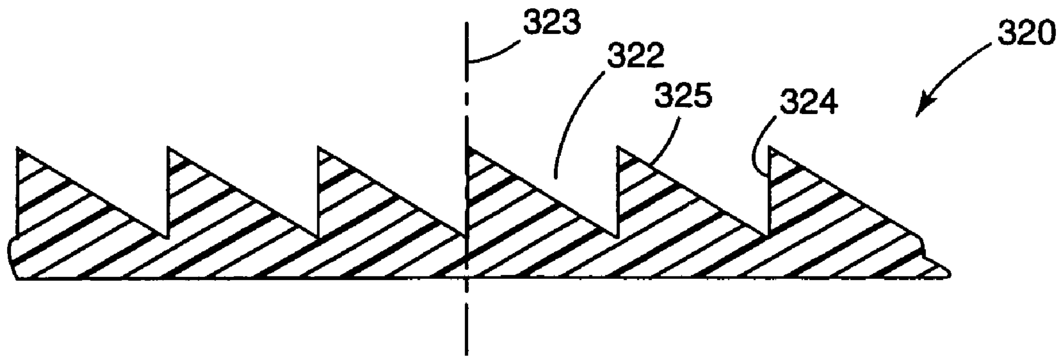
FIG. 10*b* is a partial cross-sectional view of a detection article in accordance with the present invention having V-shaped channel canted at an angle such that one sidewall of each channel is parallel to the normal.

A second method is to cant the included angle of the channels away from the normal. That is, angle the centerline of the included angles away from the normal of the film layer microstructured surface. Referring now to FIG. 10*a*, a fluid control film layer 310 is shown having a plurality of V-shaped channels 312, each with included angle Alpha. In this embodiment, the centerline of the included angle 314 is configured at a cant angle Phi from the normal 313 relative to the microstructured surface 311. Although such canting of the channel angles increases the range of incident angles that will undergo TIR from a first sidewall of a channel 312, it decreases the range of angles that will undergo TIR from the other sidewall of the channel 312 and, thus, increases light transmission through the film layer 310. As shown in FIG. 10*b*, if one of the sidewalls 324 of the channels 322 is parallel to the normal 323 of the microstructured surface of the film layer 320, and the other sidewall 325 is at less than the TIR angle (i.e., less than the critical angle), the film will be fully transmissive and will act only as a turning film through refraction, that is, the film 320 will bend the light as it passes through the film 320. It is to be understood, however, that optical transmission is usually dependent on the view point of the observer, such that canting of the channel angles may improve transparency in one direction but may reduce transparency in another direction.

Figure 10C:
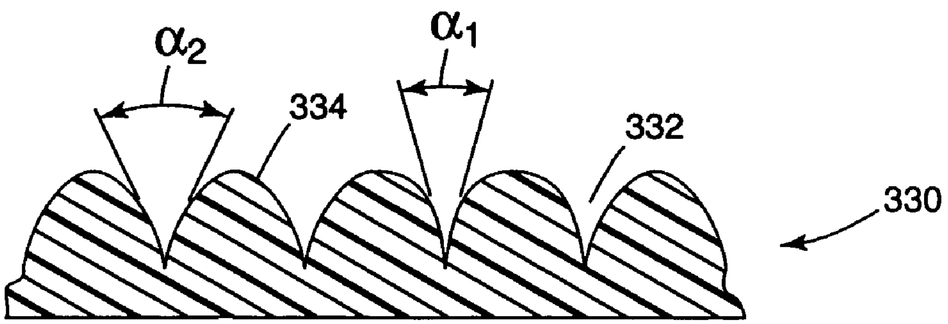
FIG. 10*c* is a partial cross-sectional view of a detection article in accordance with the present invention including convexly curved channels.

A third method of circumventing the problem is to use channels that do not have planar sidewalls. Referring to FIG. 10*c*, if a fluid control film 330 has channels 332 shaped more like an inverted Eiffel Tower than an inverted pyramid, light striking more of the surface of the sidewalls 334 would be transmitted. The surface would tend to act like a cylindrical lens. Good wicking properties of the film layer 330 would be maintained because the included angle Alpha of each channel 332 will vary and, although a portion of the channel 332 will have a wide included angle, such as Alpha 2, at least a portion of the channel 332 will have narrow included angle, such as Alpha 1. In addition, good volume capacity would be maintained because the channels 332 widen at the surface 331.

Referring again to FIG. 8, optical enhancement of the cap layer 265 may be provided only in the detection zone, in a viewing region or as a window. Optionally, the entire cap layer 265 may be optically enhanced to aid in viewing fluid flow throughout the entire detection article 260. Alternatively, the fluid control film layer, such as 261, may be optically enhanced for various reasons and used with or without cap layer 265. Reasons for optical enhancement of the fluid control film layer 261 may include the desire to view through the film layer 261 to see an identifiable graphic, color or item of text, such as brand image or name, model number, applicable range data, or other such information that may be important to a user and the test being run. Another reason may be to observe the fluid flow within the detection article 260 to verify adequate filling of the article 260 prior to the test being analyzed, to ensure proper results. Another reason may be the inclusion of a dye or colorant in the film layer 261 to aid in detection, which, unfortunately, tends to adversely affect the light transmission through the film layer 261. Still another reason may be to view detectable characteristics in various layers of a multi-layer stacked detection article (not shown). Other reasons for optical enhancement may be apparent to one of skill in the art.

In a like manner, it may be beneficial to provide optically enhanced microstructured fluid control film for microfluidic processes and/or devices other than the detection articles described herein. These processes and/or devices may include passive or active fluid transport or fluid control. Applications may include, for example, diapers, pads, absorbent mats, bandages, wound management devices, drains, drapes, vacuum devices, filters, separation media, heat exchangers, liquid dispensing devices, and other microfluidic devices for the testing and/or handling of fluid samples. Such applications may be usable with physiological fluids, as described above, and/or with other fluids, such as hydraulic fluid, lubricating fluids, natural and/or synthetic fluids, or the like, or in any microfluidic device, with any fluid wherein optical enhancement of the device would be beneficial.

Referring now to FIG. 11, a detection article 400 of the present invention is illustrate that includes a fluid control film layer 402 including adjacent coextensive channels 404 that permit the transport of a fluid from an acquisition zone 410 to a detection zone 420. In addition, a cap layer 408 is provided that substantially fully covers the channels 404 of the film layer 402. The detection article 400 may be in the form of a “dip stick” type article and may optionally include a handle portion 405 to facilitate, for example, the positioning or dipping of the acquisition zone 410 into a fluid sample. In this embodiment, the detection zone 420 includes an “open” window 421 formed as a rectilinear aperture in the cap layer 408. The window 421 provides access to the channels 404 of the detection zone 420, as well as unobstructed observation of the characteristics of the test or tests run within the detection article 400. This article 400 may be configured for simultaneously performing a multiplicity of tests, for example, chemical or biochemical tests, wherein each channel 404 contains a unique assay reagent. The assay reagent provided in each channel 404 may be a different test reagent or a concentration gradient of the same reagent. The assay reagents may be dried solids that are rehydrated when the acquisition zone 410 contacts a test solution, which is wicked into the channels 404 and comes into fluid contact with the dried solids. Alternatively, the assay reagents may be contained in a hydrogel which occupies the entire volume of at least a portion of the length of the channels 404, or only a portion of the volume of one or more channels 404. The assay reagents may also be covalently anchored to the surface of one or more channels 404, or may be coated onto or anchored to the surface of a physical support structure provided within one or more channels 404 (as described in more detail below).

Figure 14B:
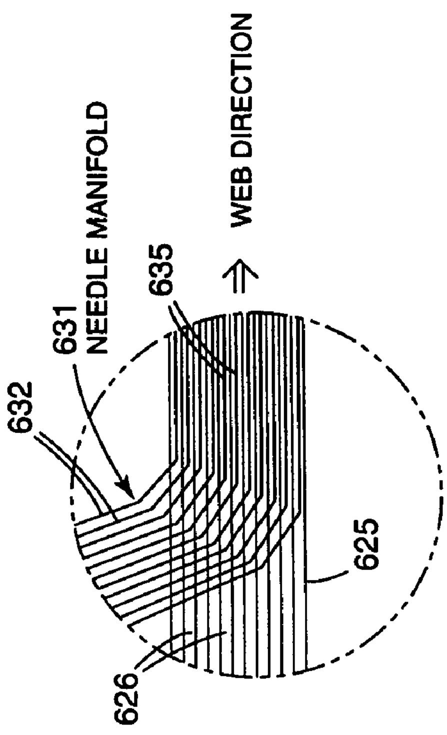
FIG. 14*b* is an enlarged view of a portion of the process shown in FIG. 14*a*.
Figure 14A:
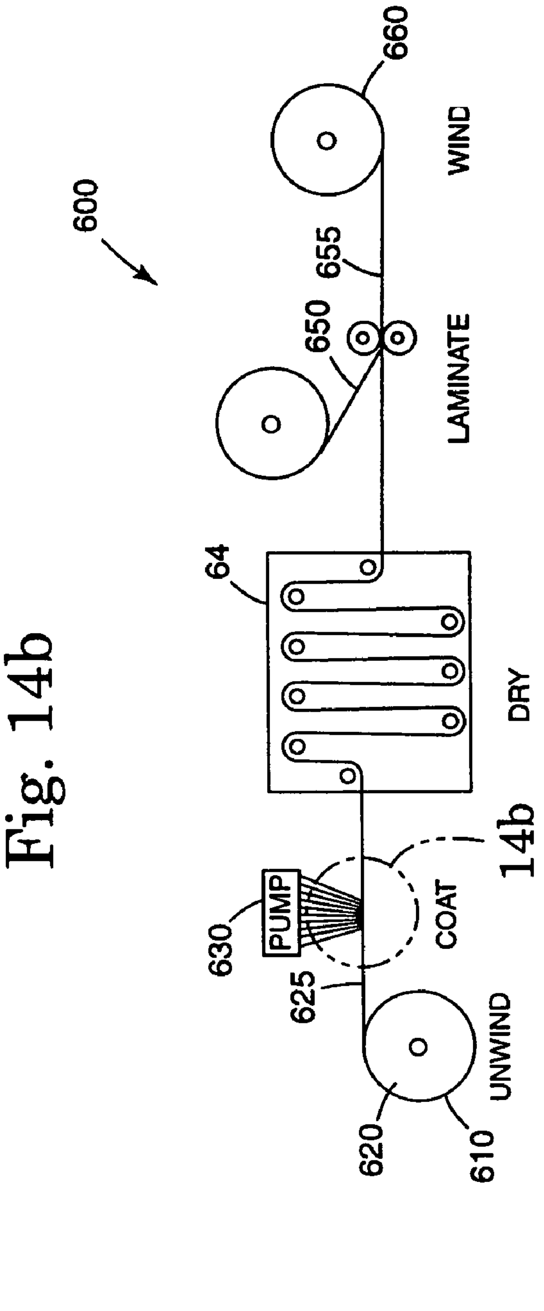
FIG. 14*a* is a diagram of one manufacturing process for producing detection articles in accordance with the present invention.

Referring now to FIG. 14, a method for manufacturing the detection article 400 described above is shown as a continuous process 600. An unwind 610 provides a continuous roll 620 of microstructured fluid control film 625 that includes a plurality of discrete microstructured channels 626 of a desired cross-sectional configuration. A pumping system 630 includes a needle manifold 631 having a plurality of needles 632 that serve to deliver a unique reagent 635 or other desired material into the parallel channels 626 of the fluid control film 625. The reagents 635 provided may differ from channel to channel, may alternate channels or may be the same in particular channels, as desired. A drying system 640 is provided to dry the material placed within the channels 626, if needed, and then an optional cap layer 650 may be laminated over the open channel surface, if desired. The finished detection article web 655 is then wound at a winding station 660 for later converting, such as by slitting into strips to form miniature diagnostic devices.

Figure 12:
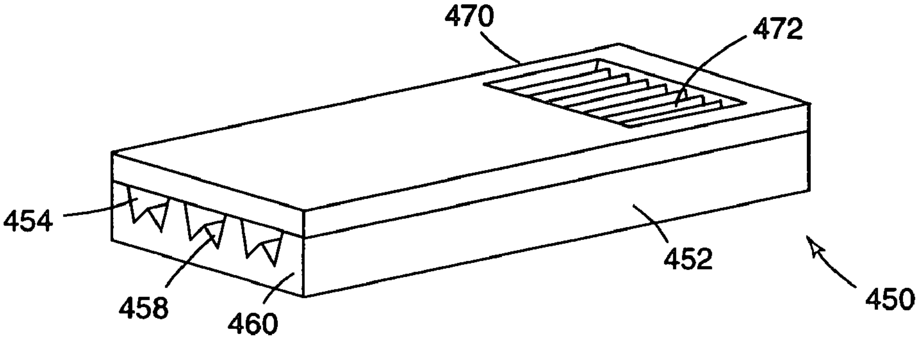
FIG. 12 is a perspective view of another detection article in accordance with the present invention including a fluid control film layer and a cap layer.

Referring now to FIG. 12, another embodiment of a detection article 450 of the present invention is shown including a fluid control film layer 452 having coextensive channels 454 that facilitate the transport of fluid from an acquisition zone 460 to a detection zone 470. The detection article 450 also includes a cap layer 456 that has a closed but transparent window 472 positioned within the detection zone 470. In this embodiment, the channels 454 include conductive material 458, shown provided throughout the length of the channels 454, to facilitate dielectric detection within the detection zone 470. If provided with a fully transparent cap layer 456 to allow observation of the test characteristics throughout the length of the article 450, the detection zone 470 could be said to overlap the acquisition zone 460 extending across the length of the detection article 450.

Figure 13A:
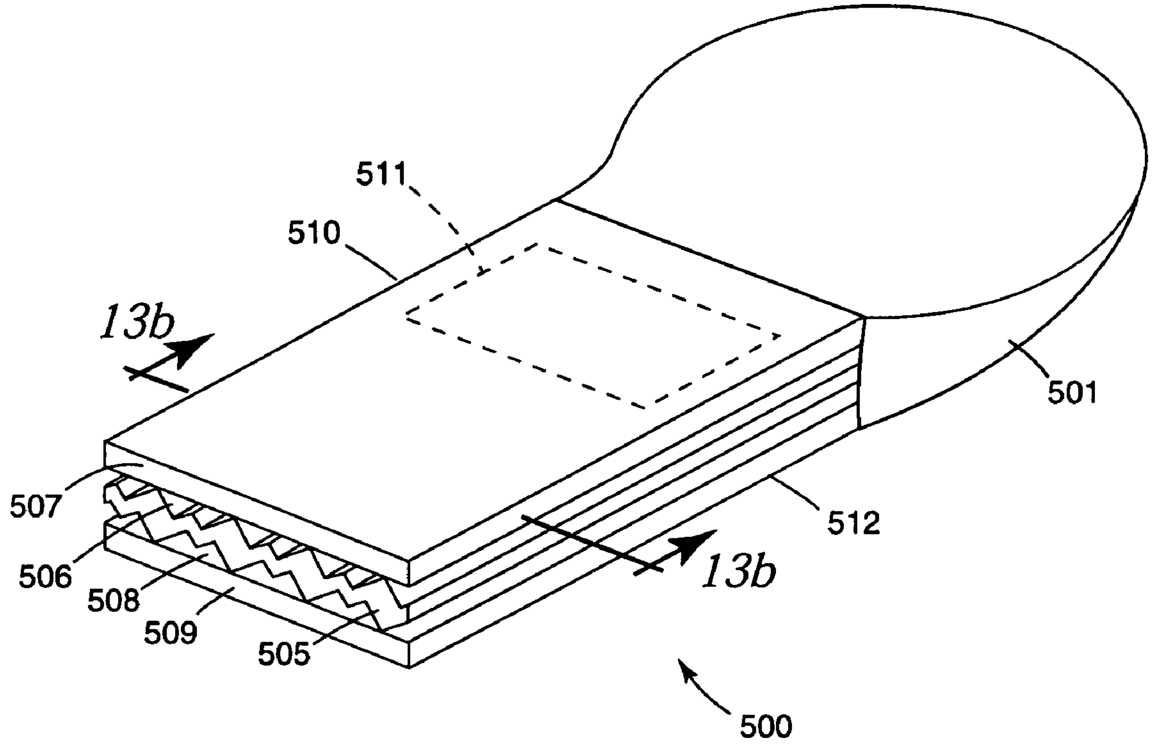
FIG. 13*a* is a perspective view of yet another detection article in accordance with the present invention including a fluid control film layer having a microstructured surface on both sides of the layer, two cap layers and a handle.
Figure 13B:
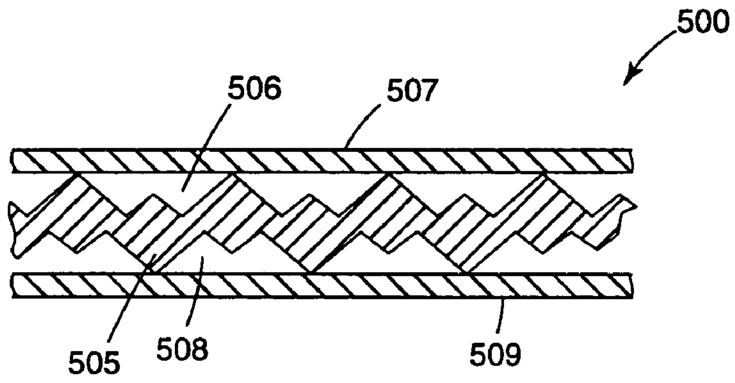
FIG. 13*b* is a partial cross-sectional view of the detection article of FIG. 13*a*.

Referring now to FIGS. 13*a* and 13*b*, in yet another embodiment of the present invention, a double detection article 500 is shown formed as a dip-stick having a handle 501. The detection article 500 includes a fluid control film layer 505 configured with channels 506, 508 on both side of the layer 505, similar to layer 112*i* shown in FIG. 1*i*. The article 500 also includes two cap layers 507, 509 provided to enclose the channels 506, 508, respectively. Detection zones 510, 512 for each side of the film layer 505 are provided with viewing regions, such as 511 shown for cap layer 507. As with other cap layers described above, the viewing region 510 may be configured as an open window, closed and transparent window, a transparent cap layer or other suitable configuration. The detection zones 510, 512 may include one type of detection element that is the same for both zones 510, 512, or may include one type of detection element that differs for both zones 510, 512, or may include a plurality of detection elements that are the same or different for both zones 510, 512. In addition or alternatively, the detection article 500 may include one type of assay reagent located inside or outside the detection zones 510, 512 that is the same for both sides of film 505, or may include one type of assay reagent located inside or outside the detection zones 510, 512 that is different for both sides of film 505, or may include a plurality of assay reagents that are the same or different for both sides of film 505. The double detection article 500 allows for multiple simultaneous tests to be run on a sample and then detected with a single acquisition of sample liquid, thereby providing even greater versatility and speed for sample testing.

In yet another embodiment, a physical support can be employed for facilitating detection of a target material. Physical supports useful with articles of the present invention include, but are not limited to threads, beads, porous media or gels. These supports may be placed within one or more channels of a detection article and serve as a capture site for target material. These supports are preferably located within the detection zone of the article, but may also be located outside of the detection zone, if desired to aid in sample preparation for later detection within the detection zone. One or more assay reagents may be covalently anchored to the physical supports provided, or may be otherwise immobilized on a support (i.e. either directly by adsorption or through a linking group) to form a sensing composite structure within the detection zone of the article. Free-standing membranes may be formed from various polymers including polyethylene, polypropylene, polyvinylidene chloride, polyvinyl chloride (PVC), polysulfone, cellulose, functionalized cellulose, and nylon, and from silica, such as a silica xerogel or porous glass. Useful substrates are preferably permeable to ions and to the biological molecules of interest. One example of a preformed support is alpha cellulose in the form of a cotton lint paper. A second example of a support is hydrophilic porous polypropylene coated with PVC as described in PCT patent publication WO 92/07899, which is herein incorporated by reference in its entirety. A third example is hexanediamine-functional cellulose as described in U.S. Pat. No. 5,958,782, which is herein incorporated by reference in its entirety. A fourth example is dimethyl azlactone functional polymers.

Figure 15:
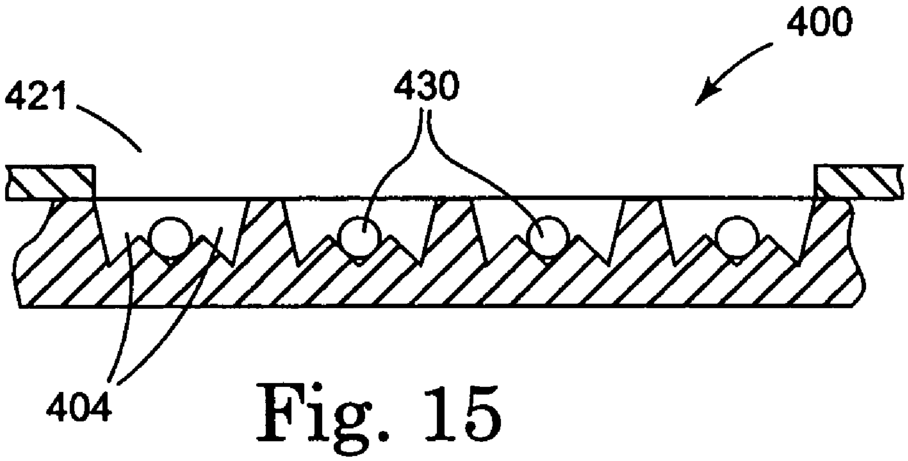
FIG. 15 is a partial cross-sectional view of the detection article of FIG. 11 including a physical support, such as a thread, located within each channel.

Referring again to FIG. 11, as well as to a cross-section of article 400 shown in FIG. 15, the detection article 400 may include a minute piece of thread 430: placed with a groove of one or more of the channels 404. The thread 430 provides a support that presents a probe for target capture. The available surface area and flow disruption cause by the thread 430 may provide an improved means for rapid detection with a high signal to noise ratio. The thread 430 may extend along the entire length of the article or may extend within the detection zone 420 only a short distance determined to be sufficient to provide the target capture desired. Optionally, the physical support within the channels may be provided by another microstructured surface, such as a microstructured cap layer (not shown), that mates into the channels as needed. This would facilitate the physical separation of the support by removal of the support layer, for subsequent storage or processing.

Figure 16:
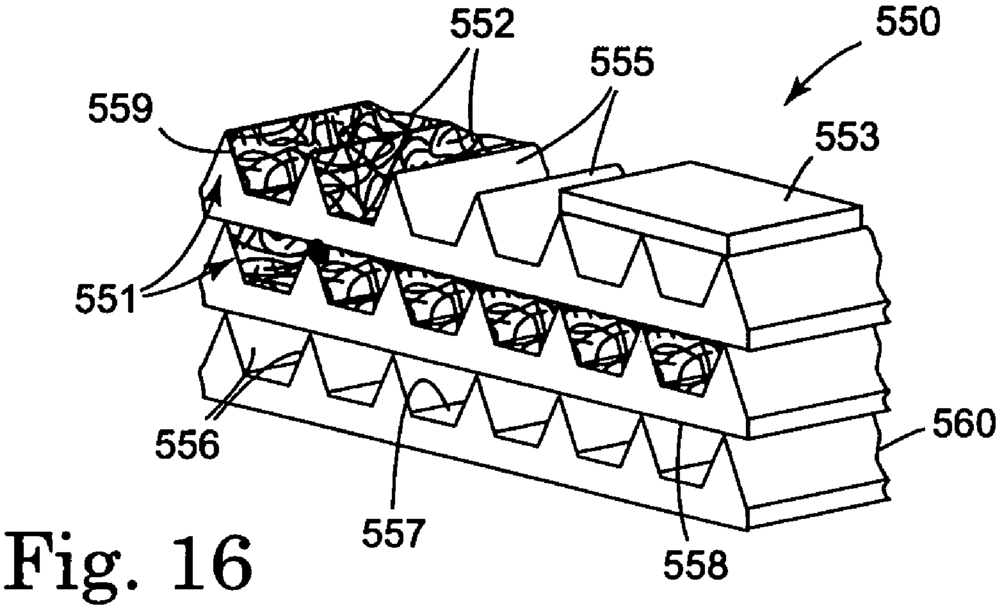
FIG. 16 is a perspective view of a three-dimensional detection article including binding zones formed within each enclosed channel.

Referring now to FIG. 16, in still another embodiment, an article 550 formed as a three-dimensional array of biological probe binding zones may be provided. A stack of microstructured layers 551, each including a plurality of channels 552, is shown in which each channel 552 contains a binding zone 555, such as a hydrogel. The binding zones 555 may completely fill the volume of the enclosed channels 552 (as shown), or the binding zones 555 may be formed partially on one or more sides of the enclosed channels 552, such as sidewalls 556 or channel base 557. The binding zones 555 may contain a biomolecule such as an oligonucleotide, enzyme, or antibody, or may contain a reporter molecule such as a fluorogenic or chromogenic enzyme substrate. The binding zones 555 are retained in position and isolated from adjacent binding zones 555 by physical barriers, including the sidewalls 556, the channel base 557, and lower surface 558 of an adjacent layer 551 or a cap layer 553. Preferably, each binding zone is open at its ends, such as front face 559 and rear face 560, providing for the efficient passage of solution through the binding zones 555.

In preferred embodiments, this type of three-dimensional array article 550 of the present invention overcomes the speed and sensitivity limitations of the prior art arrays. The article 550 preferably accomplishes this by providing discrete three dimensional gel zones 555 that are isolated from each other by physical barriers formed by the microstructured channels 552. The channels 552 provide a diffusion barrier to soluble reporter molecules, allowing for the use of enzyme-linked detection. This increases sensitivity over detection using only fluorescently labeled targets. The gel zones 555 are preferably open at their ends 559, 560, allowing solution to move through the zones 555 by capillary action. Alternatively, fluid may be passed through the gel zones 555 utilizing positive or negative pressure. Electrophoresis may also be used to facilitate rapid diffusion of biomolecules into the gel zones 555. By utilizing these methods, the hybridization and wash steps are not limited by the rate of diffusion of target solution into the gel 555. Because of this, longer path-length gel zones 555 can be utilized, again resulting in increased detection sensitivity.

Numerous applications for the detection articles of the present invention are possible. Some of the possible applications, as set forth below, help illustrate various possible compositions for assay reagents and/or sample purification materials, as well as possible detection methods and mechanisms. One particularly relevant application of the article of this invention is in the detection and differentiation of bacteria. Growing microcolonies will often excrete extracellular enzymes. In one embodiment, these enzymes can be detected using fluorogenic or chromogenic enzyme substrate indicators located in the detection zone of the article. Such indicators have a fluorescent or calorimetric dye that is covalently linked to a biological molecule that the enzyme can recognize. When the enzyme cleaves the covalent linkage, dye is release, allowing the fluorescent or calorimetric properties of the dye to be detected visually or measured spectrophotometrically. The enzyme can convert upwards of a million fluorescent indicator molecules per enzyme molecule. Because the fluorescence detection method is extremely sensitive, this provides a method to amplify the signal from a growing microcolony so that it can be detected in a short period of time.

An example where such articles are useful is in the detection of *E. coli* and coliforms in food samples. *E. coli* is an important indicator of fecal contamination in environmental and food samples, while coliform count is an important indicator of bacteriological contamination. In the quality control of water and food, it is highly important to examine for both coliform count and *E. coli*. Using an article of the present invention, one can test for coliforms in a first detection zone using a 4 methyl umbelliferone (4-MU) derivative specific for detecting β-D-galactosidase β-Gal) activity. This substrate is 4-methylumbelliferyl-β-D-galactoside (β-Gal), which is hydrolyzed by β-Gal, liberating blue fluorescent 4-MU. In a second detection zone, one can test for *E. coli* using a 4-MU derivative specific for detecting β-D-glucuronidase (β-Gud) activity. This substrate is 4-methylumbelliferyl-β-D-glucuronide (MUGud), which is hydrolyzed by β-Gud, again liberating 4-MU. For selective detection of *E. coli* in a primary isolation media, one can first perform an aerobic incubation in a selective growth medium that inhibits growth of gram-positive strains. In this way, β-Gud activities from strains other than *E. coli* are suppressed. Additionally, incubation at 44° C. and detection of gas formation help in exclusive detection of *E. coli.*

A detection article of the present invention and comprising a panel of different fluorogenic enzyme substrates localized in each of the detection zones may also be used to advantage to detect or identify an unknown microorganism based on a determination of its enzyme activity profile. Many enzymes have been identified which are specific to particular groups of bacteria, and it is likely that other enzymes will be identified in the future that demonstrate such specificity (see generally, *Bergey's Manual of systematic Bacteriology,* 1989, Williams and Wilkins, U.S.A.). For example, most gram-negative bacteria exhibit L-alanine aminopeptidase activity. Coloform bacteria (a group of gram negative bacteria) additionally express galactosidase activity. *E. coli* bacteria (a species in the Coliform group) additionally express β-glucuronidase activity. The enzyme β-glucosidase is found in the *Enterococcus* group of bacteria. The *Candida albicans* yeast pathogen exhibits N-acetyl β-glucosaminidase activity.

The articles of the present invention can provide for the rapid identification of microorganisms or enzymes isolated from clinical samples, food samples, cosmetics, beverage samples, water and soil samples. Clinical samples may include urine, stools, wound, throat, genital samples, or normally sterile body fluids such as blood or cerebral spinal fluid. The microorganisms are usually isolated from the specimen prior to identification. In antibiotic susceptibility and minimum inhibitory concentration testing, an absence of enzyme activity in the presence of antibiotics, as compared to the presence of enzyme activity of a control sample, is indicative of antibiotic effectiveness. The compositions, articles and systems are useful to screen for disease states (e.g. excessive alkaline phosphatase in seminal fluid is indicative of prostate cancer; also, the activity of urinary N-acetyl β-glucosaminidase provides a sensitive measure of renal health). They are also useful for identification of an organism in a specimen. In most cases, the organisms being determined will be bacteria. However, other microorganisms such as fungi, can also be identified.

In use, a bacterial suspension is partitioned by wicking into each of several acquisition zones of the detection article. Partitioned samples wick into each of several detection zones where they incubate with each of the different fluorogenic enzyme substrates required to determine the enzyme activity profile. A detectable product is typically developed after a relatively short incubation period of 2–30 minutes. The amount of the corresponding enzyme in each subsample is then determined by spectrophotometric analysis of each detection zone.

The number of fluorogenic enzyme substrates required to identify a particular microorganism will depend on the microorganism. In some cases, a single compartment may be enough. In other cases, multiple compartments, each containing a specific fluorogenic enzyme substrate or concentration of the substrate will be required to differentiate one microorganism from another having a very similar profile. Example profiles are outlined in U.S. Pat. No. 4,591,554 and U.S. Pat. No. 5,236,827, incorporated herein by reference in their entirety.

The degree of reaction of an enzyme with each of the substrates may be determined by examination of each reaction compartment with a fluorescence detection system. In specific implementations, an initial fluorescence reading is taken as soon after inoculation as convenient. Subsequent readings are taken at periodic intervals and used to calculate rates of reaction or to determine the onset of detection for each reaction compartment. This information is transmitted to a processor assembly which compares the data to a set of standard rate data for microorganisms and determines an identification.

Articles of the present invention comprising panels of fluorogenic enzyme substrates can be used to test for a large number of common microorganisms, including without limitation the following microorganisms: *Aeromonas hydrophilia, Aeromonas caviae, Aeromonas sobria, Bacillus cereus, Bacillus stearothermophius, Bacillus subtilis, Bacillus sphaericus, Bacteroides fragilis, Bacteroides intermedium, Candida albicans, Citrobacter freundii, Clostridium perfringens, Enterobacter aerogenes, Enterobacter cloacae, Enterococcus faecium, Enterococcus faecalis, Escherichia coli, Haemophilus influenzae, Haemophilus parainfluenzae, Klebsiella pneumoniae, Lactococcus lactis, Mycobacterium fortuitum, Neisseria gonorrhoeae, Organella morganii, Peptostreptococcus anaerobius, Peptococcus magnus, Proteus mirabilis, Pseudomonas aeruginos, Pseudomonasfluorescens, Pseudomonas pudita, Salmonella typhimurium, Serratia liquefaciens, Serratia marcescens, Staphylococcus aureus, Staphylococcus epidermidis, Staphylococcus hominis, Staphylococcus simulans, Streptococcus agalactiae* B, *Streptococcus anginosus, Streptococcus constellatus, Streptococcus faecalis* D, *Streptococcus mutans, Streptococcus pyogenes, Streptococcus uberis*, and *Xanthomonas maltophilia.*

In one embodiment, a detection assembly is positioned and adapted to detect the intensity or location of emitted signal(s) from the various detection zones of the article. The output from the detection article is typically converted to a digital signal by an analog to digital (A/D) converter and transmitted to a processor assembly. The processor assembly is positioned and adapted to process and analyze the emitted signal(s) in determining the concentration, location, or enumeration of biomolecules, bio-macromolecules, or microorganisms. This processor assembly may be part of a stand-alone unit or may be part of a central computer or local area network. Optionally, the processor assembly may contain a relational data base which correlates the processed data for each sensing element with corresponding identifiers for samples or articles, e.g., a food sample, a drug sample, a clinical sample, a sterilized article, etc.

Another important application area involves the incorporation of selective binding agents in the detection zone(s) for use in clinical diagnostic and high throughput screening applications. In this format, a target biomolecule is detected using a capture probe (e.g. an antibody or DNA probe) that is anchored to a specific location within the detection zone. As sample is wicked from the acquisition zone into the detection zone, the target biomolecule is selectively captured by the capture probe. A primary or secondary detection reagent (e.g. an antibody or a DNA probe that is labeled with a fluorescent, phosphorescent, radioactive or other detectable species) also binds selectively to the target. After unbound reagents are wicked from the detection zone, the signal associated with the detection reagent is determined. In the case of an Enzyme-Linked Immuno-Sorbant Assays (ELISA), an enzyme conjugated antibody reporter probe is introduced that binds to the captured targets. The retained enzyme activity is detected using a fluorogenic enzyme substrate.

Homogeneous immunoassay techniques are generally more rapid and convenient than their heterogeneous counterparts for use in the detection article of the present invention. In this assay format, each detection zone has associated with it a fluorogenic enzyme substrate that is conjugated to a macromolecular substrate identical to the biological target molecule under assay. In this case, the sample target and conjugated target (having the fluorogenic enzyme substrate) compete for binding to a fixed pool of antibodies within the individual detection zones. Once the antibodies bind to the conjugated target, they inhibit access of added enzyme, and the fluorogenic enzyme target is protected from cleavage. As the amount of sample target increases, the number of antibodies available to protect the conjugate target decreases, and the fluorescent signal from enzymatically cleaved conjugate increases. The amount of sample introduced into each detection zone can be varied through design of the acquisition and/or detection zone geometries. U.S. Pat. No. 4,259,233 teaches the use of β-galactosyl-umbelliferone-labeled protein and polypeptide conjugates in immunoassays.

Examples of homogeneous immunoassays detectable using articles of this invention include those for hormones such as insulin, chorionic genadotropin, thyroxine, lithyromine, and estriol; antigens and haptens such as ferritin, bradykinin, prostaglandins, and tumor specific antigens; vitamins such as biotin, vitamin $B_{12}$, folic acid, vitamin E, vitamin A, and ascorbic acid; metabolites such as 3',5'-adenosine monophosphate and 3',5'-guanosine monophosphate; pharmacological agents or drugs, particularly those described below; antibodies such as microsomal antibody and antibodies to hepatitis and allergens; and specific binding receptors such as thyroxine binding globulin, avidin, intrinsic factor, and transcobalamin.

These types of assays are particularly useful for the detection of haptens (and analogs thereof) of molecular weight between 100 and 1000, particularly drugs and their analogs, including the aminoglycoside antibiotics such as streptomycin, neomycin, gentamicin, tobramycin, amikacin, kanamycin, sisomicin, and netilmicin; anticonvulsants such as diphenylhydantoin, phenobarbital, primidone, carbamazepine, ethosuximide, and sodium valproate; bronchodialators such as theophylline; cardiovascular agents such as quinidine and procainamide; drugs of abuse such as morphine, barbiturates and amphetamines; and tranquilizers such as valium and librium.

Polypeptides that can be detected with articles of the present invention include angiotensin I and II, C-peptide, oxytocin, vasopressin, neurophysin, gastrin, secretin, glucagon, bradykinin and relaxin. Proteins that can be detected include the classes of protamines, mucoproteins, glycoproteins, globulins, albumins, scleroproteins, phosphoproteins, histones, lipoproteins, chromoproteins, and ticleoproteins. Examples of specific proteins are prealbumin, $a_1$-lipoprotein, human serum albumin, $a_1$-acid glycoprotein, $a_1$-antitrypsin, $a_1$-glycoprotein, transcortin, thyroxine binding globulin, haptoglobin, hemoglobin, myoglobin, ceruloplasmin, $a_2$-lipoprotein, $a_2$-macroglobulin, β-lipoprotein, erythropoietin, transferin, homopexin, fibrinogen, immunoglobulins such as IgG, IgM, IgA, IgD, and IgE, and their fragments, e.g., $F_c$and $F_{ab}$, complement factors, prolactin, blood clotting factors such as fibrinogen and thrombin, insulin, melanotropin, somatotropin, thyrotropin, follicle stimulating hormone, leutinizing hormone, gonadotropin, thyroid stimulating hormone, placental lactogen, intrinsic factor, transcobalamin, serum enzymes such as alkaline phosphatase, lactic dehydrogenase, amylase, lipase phosphates, cholinesterase, glutamic oxaloacetic transaminase, glutamic pyruvic transaminase, and uropepsin, endorphins, enkephalins, protamine, tissue antigens, bacterial antigens, and viral antigens such as hepatitis associated antigens (e.g., $HB_1Ag$, $HB_cAg$ and $HB_eAg$).

Enzyme fragment recombination offers an alternative approach to homogenous assays in detection zones of the present invention. Genetically engineered fragments of β-galactosidase enzyme derived from *E. coli* are known to recombine in vitro to form active enzyme. This reaction can be used as a homogeneous signaling system for high-throughput screening. In this type of assay, a biological ligand such as a drug is conjugated to one of the enzyme fragments. The ligand alone does not adversely affect enzyme fragment recombination. However, if an antibody, receptor or other large biomolecule is added that specifically binds to the ligand, enzyme fragment recombination is sterically impeded and enzyme activity is lost. In this format, the detection zone contains ligand-enzyme fragment conjugate and free receptor in a dried form. Hydration by the sample leads to competitive binding of the receptor by the target ligand and by the ligand-enzyme conjugate. Receptor binding efficiency to the ligand is determined from the kinetics of enzymatic cleavage of added fluorogenic enzyme substrate.

The concentration of glucose and lactate in the blood is extremely important for maintaining homeostasis. In a clinical setting, accurate and relatively fast determinations of glucose and/or lactate levels can be determined from blood samples utilizing electrochemical sensors. In one embodiment of a glucose measuring device of the present invention, the detection zone comprises an electrochemically based glucose detection element. Sample is taken up by the acquisition zone and channeled to one or more detection zones comprising modified enzyme electrodes. In one preferred embodiment, the electrodes have a base layer comprised of microflex circuitry printed on the fluid control film or on the cover layer. The microflex traces may nominally be made of copper and serve to connect the active electrodes in the detection zones with a meter configured and adapted to detect the concentration of glucose based on an amperometric reading from the electrodes. The reference electrode is preferentially coated with silver and the substrate electrode is preferentially coated with gold.

The working electrode is coated with an enzyme capable of oxidizing glucose, and a mediator compound which transfers electrons from the enzyme to the electrode resulting in a measurable current when glucose is present. Representative mediator compounds include ferricyanide, metallocene compounds such as ferrocene, quinones, phenazinium salts, redox indicator DCPIP, and imidazole-substituted osmium compounds. Working electrodes of this type can be formulated in a number of ways. For example, mixtures of conductive carbon, glucose oxidase and a mediator have been formulated into a paste or ink and applied to a substrate as described in U.S. Pat. Nos. 5,286,362 and 5,951,836. Additionally, multiple layer printing and analyte selective membrane layers may be required to optimize the electrode performance as discussed in U.S. Pat. No. 5,529,676.

In an alternate embodiment of the glucose measuring device of the present invention, the detection zone comprises a calorimetric sensing element. This sensing element is comprised of a hydrophilic membrane, such a nylon membrane, and reagents useful in performing a colorimetric determination of glucose concentration. In this embodiment, the membrane contains glucose oxidase, peroxidase, 3-methyl-2-benzothiazoline hydrazone hydrochloride (MBTH) and 3-dimethylaminobenzoic acid (DMAB). Sample is wicked from the acquisition zone into the detection zone. In the detection zone, the glucose present in the blood is consumed by the glucose oxidase in a reaction which generates hydrogen peroxide. The hydrogen peroxide is consumed by the peroxidase enzyme in the presence of the MBTH-DMAB couple to produce a light absorbing product with an absorbance maximum at approximately 635 according to known chemistry (see U.S. Pat. No. 5,179,005). Reflectance measurements of the reaction zone of an inoculated channel can be used in determining the concentration of glucose in the test strip. The accuracy of the determination can be improved using an array of reaction zones corresponding to different volumes of sample or different concentrations of reagents and making use of all of the available data.

In yet another embodiment of the glucose sensor of the present invention, the detection zone comprises a fluorescence based glucose detection system. In this embodiment, fluorescent based oxygen sensor such as that described in U.S. Pat. No. 5,409,666 is coated with a membrane layer comprising glucose oxidase. In the detection zone, the glucose and oxygen present in the sample are consumed by the glucose oxidase. This depletes the oxygen in the vicinity of the fluorescence based oxygen sensor, resulting in an increase in fluorescence. A control channel, lacking the glucose oxidase, will not show a change and can serve to provide a reference fluorescent signal. The fluorescent signals can be read using a compact LED based reader comprising lights sources, detectors and an A/D converter. The fluid control film is simply inserted into the reader and a measurement is made.

The present invention provides a rapid, convenient, and low cost device for sample testing, especially where a multiplicity of tests (e.g., biological tests) are required. The device of the present invention provides several advantages over the "array of wells" devices currently utilized in the art for a multiplicity of tests. Preferred devices of the present invention utilize a relatively small volume of the sample contained in the channels. This enables a more rapid response to biological reactions. Also, multiple pipetting of the sample into separate wells is eliminated. Each channel may be simultaneously inoculated by contacting one edge or the surface of the device to a fluid sample of interest. More preferred devices of the present invention also cost less than the aforementioned wells. Not only do they preferably use less reagent for each test, the device may preferably be manufactured in a continuous process, e.g., using a single microstructured film or a simple two-part construction of an embossed microstructured bottom film and a sealable cover film. In addition, the ability to build three-dimensional stacked structures using the microstructured fluid control film provides the ability to engineer the surface to provide fluid movement to defined locations.

EXAMPLES

The following examples are offered to aid in the understanding of the present invention and are not to be construed as limiting the scope thereof. Unless otherwise indicated, all parts and percentages are by weight.

Examples 1 and 2 described below demonstrate the utility of the multiparameter test device for two common microbiological tests. It should be appreciated by those skilled in the art of biological testing that the device of the present invention could be used in a variety of methods that are currently performed using a topical 96 well microtiter tray format.

Example 1

Bacterial Identification

Run 1a: Preparation of Embossed Films.

Films containing parallel channels were extrusion embossed onto a foam backing as described in U.S. patent application Ser. No. 08/905,481. The cross-section of each channel was in the shape of an inverted trapezoid having a base of approximately 0.75 mm and a height of approximately 1.0 mm. The sidewall angle was approximately 15 degrees. Each channel was separated by a "land area" of approximately 0.75 mm. The channels were sealed with a top film (ScotchPak #6, 3M Company) using a roll-to-roll laminator station heated to 149 degrees C. (300 degrees F.).

Run 1b: Substrate Profile Determination.

A commercial ID kit (BBL Enterotube II, Becton Dickenson Co.) containing the 12 tests outlined in Table 1 was used for comparison to the microchannel device. The hydrogel from each compartment of the ID kit was removed with a spatula and placed in a test tube. The hydrogel was melted by placing the tubes in a heated block at approximately 88° C. (190° F.). The melted gel was removed from the test tube with a transfer pipette. The tip of the pipette was placed into the opening of a microchannel formed from an embossed film and cover as described above. The gel was dispensed into the channel and allowed to cool. This procedure was repeated to fill adjacent microchannels. After all 12 channels were filled, the film was cut into 2.54 cm (1 inch) strips perpendicular to the direction of the channels.

A suspension of *Escherichia coli* ATCC 51813 was prepared using a Prompt inoculation system (Baxter Healthcare Corporation, Microscan Division, W. Sacramento Calif.) according to the manufacturer's instructions. The final concentration of bacteria was $10^5$ per milliliter. Approximately 10 milliliters of the bacterial suspension was poured into a sterile basin (Labcor Products, Frederick Md.). One edge of the microchannel device was dipped in the solution, contacting the gel at the end of each channel. A control was also inoculated in this manner using sterile buffer. The experiment and control were placed flat inside a humidified petri dish and incubated for 16 hours at 37° C. The Enterotube II was inoculated and incubated according to the manufacturer's instructions.

The substrate profile as determined by the microchannel device was determined by color changes in each channel relative to the control device. This was compared to the commercial kit, with the results obtained in Table 1 below ("+" denotes a color change). The substrate profile determined by the microchannel device was in agreement with the Enterotube II profile.

TABLE 1

| Test | Microchannel Device | Enterotube II |
|---|---|---|
| Glucose | + | + |
| Lysine | + | + |
| Ornithine | + | + |
| H2S/Indole | Not determined (ND) | (ND) |
| Adonitol | − | − |
| Lactose | + | + |
| Arabinose | + | + |
| Sorbitol | + | + |
| Vogues-Proskauer | ND | ND |
| Dulcitol/PA | + | + |
| Urea | + | + |
| Citrate | − | − |

Example 2

Minimum Inhibitory Concentration (MIC) Test

Run 2a: Preparation of Microchannel Films.

Microchannel polyethylene films were heat embossed on a hydraulic press according to the procedure outlined in U.S. patent application Ser. No. 08/905,481. The channels used for this experiment had a rectangular cross-section of approximately 0.087 mm (0.022 inches) deep by approximately 1.96 mm (0.077 inches) wide. The channels were covered with ScotchPak #33 (3M Company) using an iron heated to 149 degrees C. (300 degrees F.), forming a series of capillary channels.

Run 2b: MIC Test Using Microchannels.

A dilution series of tetracycline was prepared in VRB media (7.0 g Bacto peptone, 3.0 g yeast extract, 1.5 g bile salts per liter) containing the fluorescent indicator methylumbelliferyl glucuronide (MUG, 0.5 mg/ml). The following tetracycline concentrations were prepared: 40, 4, 0.4, 0.04, and 0.004 micrograms/ml. Approximately 1 ml of each solution was placed in a test tube. A suspension of *Escherichia coli* ATCC 51813 (100 microliters of approximately 107 bacteria/ml) was added to each tube. A syringe was used to transfer each solution into adjacent microchannels (1.6 microliters/channel). Both the control tubes and the microchannel device were incubated for 16 hours at 37° C. After incubation the samples were observed under ultraviolet radiation. Fluorescence was observed in both the control tubes and the microchannels in the solutions containing 0.4, 0.04, 0.004 micrograms/ml tetracycline. No fluorescence was observed in the 40 and 4 micrograms/ml samples, indicating that the minimum inhibitory concentration in this example was 4 micrograms/ml.

Example 3

Gel Arrays Formed from Sheets of Microchannel Film

Run 3a: Preparation of Microchannel Film

Microchannel film was extrusion embossed according to the procedure of Johnston (U.S. Pat. No. 5,514,120). For the examples cited below two embossing tools were used. Tool 1 produced microchannel film with a "V channel" cross-sectional profile. The microchannels had a triangular cross-section with a base of approximately 0.3 mm and a height of approximately 0.35 mm. Tool 2 produced microchannels with a square cross-section approximately 0.2 mm by 0.2 mm. In addition, the microchannels from tool 2 produced a set of 4 smaller "nested" channels (~50×50 microns) at the base of each microchannel.

Rune 3b: Preparation of Cubic Array Containing Isolated, Open-Ended Gel Zones

This run serves to demonstrate a "blank" array containing isolated, open-ended gels where each gel element is the same. To build an oligonucleotide array from such a device would require the use of a reactive gel and optionally a delivery device such as a micropippetting robot to apply modified oligonucleotides to each individual array element.

A polyethylene microchannel film containing TRITON X-35 brand surfactant (0.5% w/w) was extrusion embossed using tool 2 according to the procedure of Johnston. A section of a double-sided adhesive tape (eM, #34-7035-9513-1) was applied to the back of sections of film (1.3 cm×6 cm), with the microchannels parallel to the long dimension of the tape. Film sections containing the adhesive tape were then "stacked" in the long dimension, creating a multilayer structure containing a square array of capillary channels. If desired, the stack could be assembled using an adhesive layer (in place of the double-sided tape) or by another suitable joining method such as heat or sonic bonding. A solution of agarose (1% by weight, BioRad) was prepared by beating the solution above the melting temperature of the gel according to the manufacturer's instructions. Green food coloring was added to provide visual contrast. One open end of the multilayer capillary was placed in the solution, which was wicked into the channels by capillary action. The multilayer structure was removed from the solution and allowed to cool, solidifying the gel.

An array of open-ended, isolated gels was produced by cutting a thin section (~1 mm) from the end of the multilayer structure using a razor blade. The array contains approximately 1, 100 isolated, open-ended gel zones per square centimeter.

Rune 3c: Spiral Array Containing Isolated, Open-Ended Gel Zones.

This run describes an alternative technique for forming an array of open-ended gel zones. A strip of microchannel film backed with adhesive (e.g., a double sided adhesive tape) was prepared as described above, with the microchannels perpendicular to the long direction of the backing. The film was wound around a plastic rod (2 mm diameter) until a diameter of 7 mm was achieved, creating a spiral pattern of gel zones. The wound film was placed inside a section of heat shrink tubing and the assembly was heated with a heat gun for 15 seconds. One end of the wound film was dipped in melted agar (prepared as described above), wicking the agar into the microchannels. The assembly was allowed to cool, solidifying the gel in the channels. A disk of channels was cut from the end of the assembly.

The shape of the spiral array presents several potential advantages. Detection of hybridization using this type of structure could be performed using a CD-type optical scanning system. Also, the round array described in this example fits into the bottom of the wells in a 96 well microtiter plate. This permits approximately 500 array elements per well.

Run 3d: Preparation of Gel Array Containing Alternating Gel Zones

The above runs served to demonstrate the concept of arrays containing a "blank" set of gel zones. Oligonucleotide arrays would be built by adding modified oligonucleotides to each array element by, for example, micropippetting or inkjet printing. For manufacturing purposes, it may be advantageous to eliminate this second step by filling individual microchannels with gel-immobilized oligonucleotides. One suitable method for simultaneously filling adjacent microchannels uses a needle manifold. See FIG. 3. Sheets prepared in this manner could be stacked and cut into arrays as described above, eliminating the need to add oligonucleotides in a second microdispensing step.

A manifold with a series of syringe needles in register with the microchannels of a microchannel film was prepared as follows. A section of microchannel film from Run 3a was cut into a strip approximately 7.6 cm (3 inches) long. Twelve 15 cm syringe needles (6 inches long, 22 gauge, Fisher Scientific) were placed in adjacent channels with the tips protruding approximately 1/27 cm (½ inch) from the end of the film. A layer of epoxy adhesive (5 minute epoxy, 3M Company) was placed over the assembly and allowed to cure. Twelve aqueous solutions containing 0.25% guar were prepared. The following colors were added to the solutions using food coloring: light red, yellow, brown, dark blue, dark green, dark orange, clear, purple, light orange, light green, light blue, and dark red. The solutions were placed in 20 CC syringes, followed by loading into a 12 station syringe pump (Harvard Apparatus, South Natick, Mass.). The syringes were connected to the manifold using teflon tubing (3 mm O.D., Voltrex, SPC Technology, Chicago, Ill.).

A section of microchannel film from Run 3a was cut into a section approximately 61 cm (2 feet) long. The multisolution manifold was placed at one end of the film with the needles resting in the bottom of the microchannels. The needle manifold was held in place as the film was manually pulled underneath. As the film was being pulled, the syringe plungers were depressed at a rate sufficient to fill the microchannels without liquid—liquid communication over the "land" area. The coated film was dried at 37° C., followed by lamination of a top cover (ScotchPak #6) as described in Example 2.

Example 4

In this example, we show how the wick structure can be used as an antibody probe capture test, for bovine serum albumin.

Run 4a: Preparation of Hydrophobic Polypropylene/Polyethylene Copolymer Films

A film sample was prepared by hot embossing polypropylene in accordance with Example 3a into a tool, which microreplicated a V shaped channel having the following dimensions: 750 um (micron) deep channel, 40 degree notch.

Run 4b: Azlactone Coating of Hydrophobic Polyethylene/Polypropylene Microstructures The film samples were then coated with a 2% solution of the primer described in U.S. Pat. No. 5,602,202, diluted in cyclohexane. The coating was performed by dip coating the film into the primer solution, then drying the film for 10 minutes at 80° C. Next, the film was dip coated into a 2% solution of methylmethacrylate: vinyldimethylazlactone (70:30) in methylethylketone, and allowed to air dry for at least 30 minutes.

Run 4c: Preparation of Antibody Probe Capture Wicks Specific for Bovine Serum Albumin The films prepared as described above, were derivatized with an antibody to bovine serum albumin. Remaining azlactone sites were neutralized with horse heart myoglobin (to prevent nonspecific binding of the BSA target. Wicks were then tested for specific capture of biotin-BSA (b-BSA) conjugate. Capture was visualized using a streptavidin-alkaline phosphatase (s-AP) conjugate and 1 mM 4-nitrophenyl phosphate (4-NPP) in a standard Enzyme Linked Immuno Sorbent Assay (ELISA) format. Enzymatic cleavage of the 4-NPP by the bound s-AP gave a bright yellow color visible within the first 30 seconds. Control wicks having only azlactone coating and myoglobin block showed no color change in the ELISA assay. Antibody capture wicks not exposed to b-BSA also showed no color change in the ELISA assay. Details of this example are provided below.

Run 4d: Reaction with Glycine to Create Carboxylated Wicks.

Azlactone coated channels were reacted with 1 M glycine in standard derivatization buffer (1M Na2SO4, 50 mM EPPS, pH 8.0) to give a carboxylated surface. Microwave heating was used to speed the reaction. Samples were placed in a trough containing neutral red pH 8.0 or methylene blue in $H_2O$/MeOH. For both indicator solutions, the channels derivatized with glycine exhibited vertical wicking the entire length of the sample (5 cm), while samples containing only the azlactone/primer, or only the primer exhibited no appreciable wicking behavior. Similar behavior was observed when the derivatization solution contained only 1 mM glycine.

Run 4e:

A variation on this experiment was to selectively derivatize alternate channels on a single substrate with antibody and demonstrate that only the alternate channels give a positive colorimetric ELISA result. This points to the ability to prepare arrays of probe capture wicks (antibody or DNA targets) where adjacent wicks are specific to different analytes.

Run 4f:

In another variation, one end of the wick array was coated with glycine, the other end with antibody, both ends were blocked with myoglobin. In this case, sample was wicked through the glycine region to the antibody probe capture region where the ELISA test gave a calorimetric response.

Run 4g:

In another variation, each of the two ends of the wick array was coated with antibody, the middle was coated with glycine, and the entire chip blocked with myoglobin. The first end was then treated with b-BSA and s-AP and washed. This end was then exposed to a BSA solution which wicked up the channels. This displaced some of the b-BSA:s-AP conjugate from the first end and recapturing it at the second end as determined by ELISA assay. In a control experiment, buffer was not nearly as effective at displacing the conjugate. This experiment illustrates the ability to displace a reporter from an antibody capture field and recapture it down stream in a competitive displacement assay.

Run 4h:

It has been discovered that one may control the rate of wicking in V-channels by varying the ratio of glycine and myglobin in the block. This can be of value in controlling the amount of material wicked into different regions of an article. This surface effect can be combined with controlling channel features as well.

Derivitization conditions: 1 mg/mL anti-BSA in derivitization buffer (1M sodium sulfate/50 mM EPPS buffer pH 8.0); react 30 minutes to overnight; wash in blocking buffer (50 mM EPPS/saline buffer pH 8.0).

Blocking conditions: 5 mg/ml horse heart myoglobin in blocking buffer; react for 30 minutes to overnight; wash with blocking buffer.

ELISA conditions: 100 ug/mL biotin-LC-BSA in AP buffer (25 mM BTP pH 8.5, 2 mM Mg++, 0.4 mM Zn++); react 30 minutes; wash with AP buffer; 2.5 ug/mL streptavidin-LC-BSA in AP buffer; react 30 minutes; wash with AP buffer; 1 mM 4-NPP in substrate buffer (1M diethanolamine buffer/0.5 mM MgC12 in pH 9.0 buffer); reaction observed visually. Pre-conjugation of biotin-LC-BSA and streptavidin-LC-BSA will speed the assay.

Example 5

Sterilization Assurance Biological Indicator Chip

Azlactone coated polyethylene/polypropylene V channels, prepared as described above, were derivatized with anti-rabbit IgG-alkaline phosphatase conjugate, blocked with myoglobin, and washed using the methods outlined above. This experiment demonstrates enzyme activity to indicate effective sterilization. The IgG conjugate is not important to the outcome, but was a convenient reagent. Samples were inserted into empty tubes with and without a filter and with and without a sorbital pretreatment of the channels. These were then exposed to brief sterilizer cycles, followed by wicking of 4-NPP in substrate buffer. The results were as follows:

TABLE 5a

| Run # | "Sterilization" cycle | Filter | Sorbitol | Result |
|---|---|---|---|---|
| 1 | 5 min @ 250 F | – | – | no activity |
| 2 | 5 min @ 250 F | + | – | no activity |
| 3 | 5 min @ 250 F | + | + | no activity |
| 4 | 2 min @ 250 F | + | – | no activity |
| 5 | 2 min @ 250 F | + | + | no activity |
| 6 | 48 hrs @ RT | + | – | bright yellow |
| 7 | 48 hrs @ RT | – | + | bright yellow |

These results indicate that enzyme activity is stable on the wicks, but is destroyed by the sterilization procedure as desired for a presumptive BI indicator. In a product, one might wish to use a more robust enzyme such as b-D-glucosidase or a carrier for such an enzyme such as *Bacillus stearothermophilus*, both of which can be covalently anchored to the wicks using the azlactone chemistry described above.

Example 6

Microchannel devices containing regions of linear solid support

This example serves to illustrate a device wherein a high surface area, linear solid support derivitized with an immobilized biological agent is incorporated into a microchannel. The linear solid support provides an efficient means for localizing a binding agent to a specific region of the microchannel. In addition, the support provides enhanced signal due to its high surface area. Finally, enhanced mixing is achieved as fluid passes through the region containing the linear support.

In the runs cited below, the linear solid support is a woven thread coated with a reactive copolymer. The copolymer contains a reactive moiety which binds to nucleophilic groups on biomolecules, for example amine functionality protein lysine residues. The coated thread is immersed in a solution containing the biological agent for a time sufficient for binding to occur. Following binding, the modified thread is placed in a microchannel. A cover is then added, creating a closed capillary structure.

Run 6a: Preparation of Linear Solid Support Containing Immobilized Enzyme

Black rayon thread (approximately 120 micron outer diameter, Coats and Clark, Inc.) was cut into sections approximately 1 cm in length. The sections were immersed in a solution of azlactone/dimethylacrylamide copolymer (30/70 wt/wt, 5% solids in isopropanol/methylethylketone solvent [20:1]) prepared by typical solution polymerization well known in the art, such as that described in U.S. Pat. No. 4,304,705, which is herein incorporated by reference. Ethylene diamine was added to the solution to a concentration sufficient to cross-link 5% of the azlactone moieties in the copolymer. After 1 hour, the threads were removed and placed in a centrifuge tube. The threads were rinsed with distilled water (3 times under sonication), sodium phosphate buffer (3 times, 50 millimolar, pH 10), and distilled water (3-times).

Enzyme was immobilized to the polymer-coated treads following the procedure outlined in Immobilized Affinity Ligand Techniques, page 95 (Academic Press, Inc., G. Hermanson, A. Mallia, P, Smith, eds., 1992). The polymer coated thread was immersed in a solution of sodium phosphate buffer (25 mM, 0.15 molar sodium chloride, 0.1% TRITON X-100 brand surfactant, pH 7.4) containing the enzyme beta-glucoronidase (100 mg/ml). After 20 minutes, the threads containing immobilized enzyme were removed and rinsed according to the procedure outlined above.

Run 6b: Demonstration of Enzymatic Activity on Coated Threads

The following run demonstrates that the beta-glucuronidase enzyme is covalently attached to the coated thread and that enzymatic activity is retained after immobilization.

Four microcentrifuge tubes were prepared as follows. Tube "A" contained the beta-glucuronidase enzyme solution described above (approximately 20 microliters). Tube "B" contained a section of thread with bound beta-glucuronidase. Tube "C" contained a section of thread that was treated with ethanolamine (50 mM in water) prior to the enzyme immobilization step. This "quenched" thread was then treated with the beta-glucuronidase enzyme according to the procedure outlined above. Tube "D" was empty.

To each tube was added 1 milliliter of a solution containing the fluorogenic enzyme substrate methylumberiferyll-beta-D-glucuronide (50 mg/ml, 50 mM sodium phosphate buffer, pH 8.5). The tubes were incubated at room temperature for 15 minutes, then observed under ultraviolet illumination (365 nanometers) for the presence of fluorescent product. The table below summarizes these results.

TABLE 6a

| Sample | Generation of fluorescent product |
|---|---|
| Tube "A"-enzyme solution | + |
| Tube "B"-enzyme bound to thread | + |
| Tube "C"-quenched thread treated with enzyme | − |
| Tube "D"-substrate with no enzyme | − |

Run 6c: Microchannel Device with Incorporated Linear Solid Support

This run serves to demonstrate that linear solid supports containing an immobilized biological agent can be incorporated into channels in a microchannel device.

A section of film prepared generally according to Run 3a containing parallel microchannels was cut to approximately 3 cm in length and 1 cm wide. The microchannels possessed a triangular cross section of approximately 300 micron base with a height of approximately 200 microns. A thread (1 cm length) treated with enzyme as described above was placed in the center region of a microchannel. To an adjacent microchannel was placed "quenched" thread (tube "C" above). A heat sealable cover film (Scotchpak film, 3M Corporation) was laminated to the top of the microchannel film using a heated iron 193° C. for 5 seconds), generating parallel "tubes" containing sections of thread. One edge of the device was dipped in a solution of the fluorogenic enzyme substrate methylumberiferyll-beta-D-glucuronide (50 mg/ml, 50 mM sodium phosphate buffer, pH 8.5), causing the channels to fill by capillary action. After 10 minutes at room temperature, significant fluorescence was observed under ultraviolet irradiation in the channel containing the thread with immobilized enzyme. No fluorescence was observed in the channel containing the "quenched" thread.

It would be appreciated by one skilled in the art that a variety of reactive coatings on the linear support which facilitate binding of biological agent could be used. Whereas the biological agent described in this example is an enzyme, a variety of biological agents could be utilized, for example an antibody, an antigen, a nucleic acid or oligonucleotide, or a carbohydrate. The example described herein could also be extended to include multiple sections of linear support placed end-to-end in a single channel. In this manner an array of binding sites could be created wherein multiple channels contain multiple regions of binding zones.

Example 7

Fluid Control Film with High Optical Transmission

In this example, it is shown how canting of the channel angles improves optical transmission through a microstructured fluid control film layer.

Run 7a:

Fluid control films designed for wicking of blood and wound exudate were produced having V-shaped channels with 99 degree included angles formed in polyolefin and polycarbonate materials. The films that did not have a hydrophilic surface, such as the polycarbonates, were sprayed with Triton™ X35 surfactant and water to make them functional fluid transport films. The channels were canted by 19.5 degrees.

A similarly formed fluid control film layer having 90 degree included angles that are not canted displays a silver-like appearance due to retroreflection of light as viewed from the normal, or head on. By canting the angle of the channels in the present example, the transparency of the film was significantly improved. Different channel depths or 4 micrometers, 8 micrometers, 16 micrometers and 24 micrometers, were evaluated and all displayed the observable improvement in optical transmission.

Run 7b:

In another variation, fluid control films having 99 degree included angle V-shaped channels formed on one major surface may be produced, which would have a specific channel depth of 24 micrometers and channel pitch of 56.20 micrometers. (See FIG. 10*a* for a representative illustration). As shown in Table 7a, while holding the channel depth and pitch constant, a number of the fluid control films could have their channels canted at increasing angles from 0 to 45 degrees. As the cant angle increased, the included angle would decrease, such that at a 45 degree cant angle the included angle would be only 74.96 degrees.

TABLE 7a

| | | | | | | | | | | |
|---|---|---|---|---|---|---|---|---|---|---|
| Cant Angle (deg.) | 0 | 5 | 10 | 15 | 20 | 25 | 30 | 35 | 40 | 45 |
| Included Angle (deg.) | 99.00 | 98.82 | 98.26 | 97.28 | 95.81 | 93.75 | 90.92 | 87.08 | 81.90 | 74.96 |

Figure 17A:
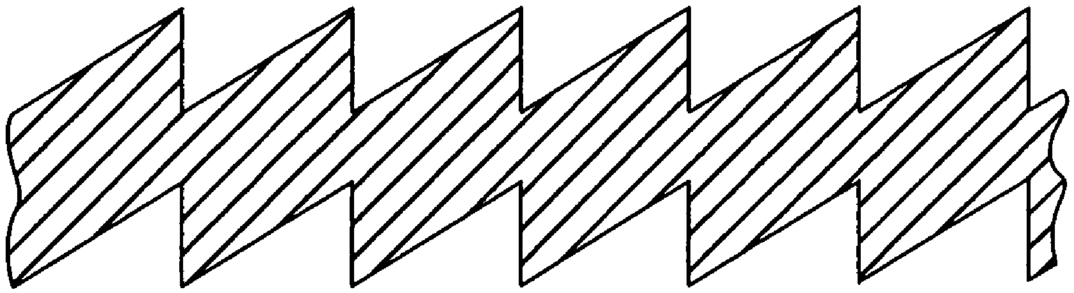
FIG. 17*a* is a partial cross-sectional view of a fluid control film layer having V-shaped channel microstructured surfaces on both sides of the film layer, wherein the channels on either side are canted in opposite directions.
Figure 17B:
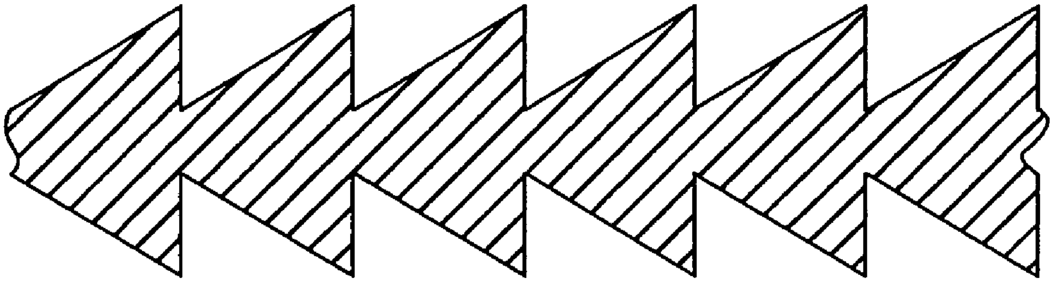
FIG. 17*b* is a partial cross-sectional view of a fluid control film layer having V-shaped channel microstructured surfaces on both sides of the film layer, wherein the channels on either side are canted in the same direction.

In a like manner, a series of fluid control films may be produced having canted channels formed on both major surfaces of the film layers. Referring now to FIG. 17*a*, in one series of films, the angles of the channels could be canted in the opposite direction. Referring to FIG. 17*b*, in another series of films, the angles of the channels could be canted in the same direction.

Figure 18A:
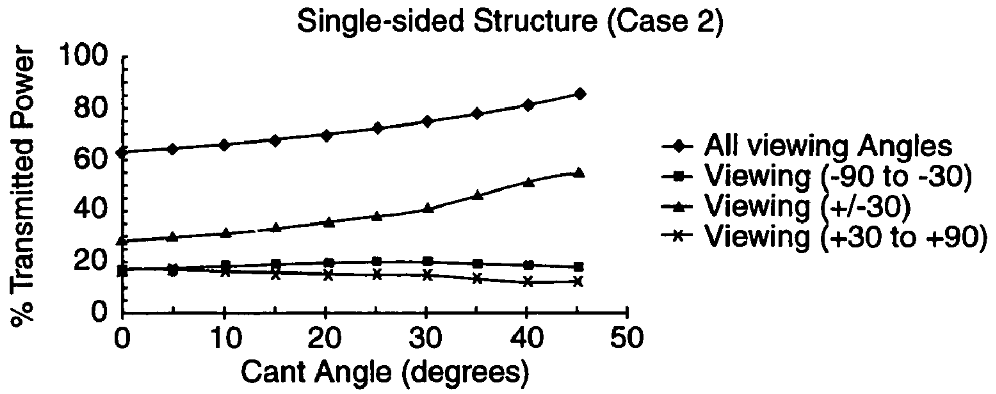
FIG. 18*a* is a plot of cant angle verses percent transmitted power for single-sided fluid control film layers having canted channels.
Figure 18B:
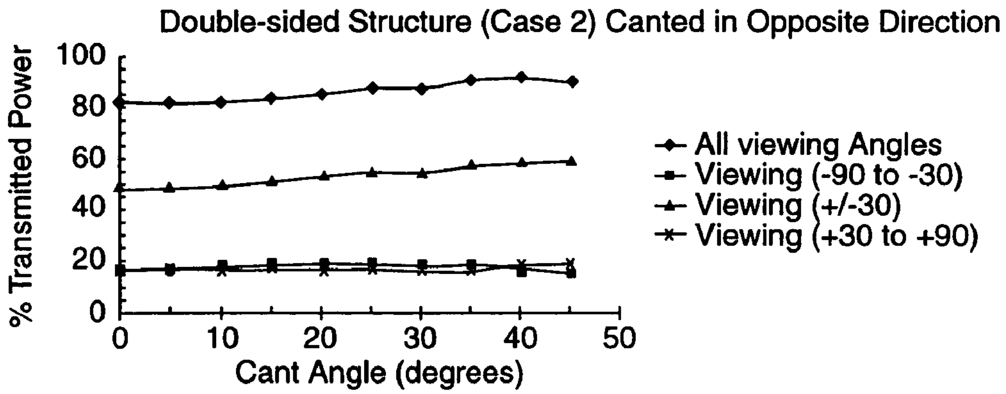
FIG. 18*b* is a plot of cant angle verses percent transmitted power for double-sided fluid control film layers having canted channels that are canted in opposite directions.
Figure 18C:
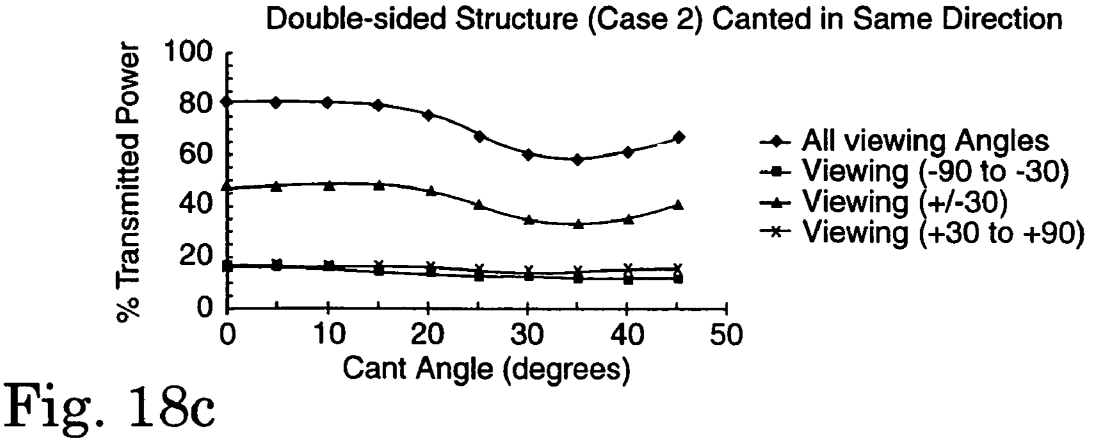
FIG. 18*c* is a plot of cant angle verses percent transmitted power for double-sided fluid control film layers having canted channels that are canted in the same direction.

The resulting series of fluid control films could then be viewed at 0 degrees (or from the normal) and from +90 degrees to −90 degrees. The percentage of transmitted light would then be recorded for each cant angle on each of the three-types of films. The results of these tests are shown in FIGS. 18*a–c*. As can be seen, a non-canted 99 degree single-sided film would transmit light at about 63 percent. This percentage would increase up to 85 percent for a 45 degree cant angle. A non-canted 99 degree double-sided film would-transmit light at about 80 percent. This percentage would rise to 90 percent at a 45 degree cant angle when canted in the opposite direction. In the third variation, a non-canted 99 degree double-sided film starting at 80 percent would fall to about 65 percent when canted in the same direction. These varying results demonstrate the variable nature of perceived light transmission based on viewpoint and angle.

Example 8

SiO2 Coating for Increased Hydrophilicity

In this example, it is shown how coating by SiO2 increases the hydrophilic nature of the fluid control film.

V groove and nested channel fluid control films were prepared by molding a poly(methylmethacrylate) film (DRG-100, Rohm and Haas) in a press using a nickel molding tool. The film and molding tool were brought into contact with each other at a temperature of 199° C. and a pressure of $3.5\times10^6$ Pascals for 15 seconds, after which the pressure was increased to $6.2\times10^6$ Pascals for a period of 10 minutes. Thereafter, the temperature was decreased to 74° C. while maintaining the pressure at $6.2\times10^6$ Pascals for a period of 15 seconds.

The polymeric substrate was then diced into individual 3 inch by 3 inch segments, referred to as chips. Portions of each chip were laminated with a Magic Mending™ Tape (3M Company) mask to cover one end of the channel array. The chips were placed onto the stage of a Mark 50 electron-beam thermal evaporation chamber. In the Mark 50, approximately 800 to 1000 angstroms of $SiO_2$ were deposited onto the microstructured surface of the chip. When the chips were removed from the chamber of the Mark 50, the masks were removed.

The microstructured surfaces of the chips were polished at the top surface and laminated with 3M # 355 (3M Company) box sealing tape applied with a nip roller to create wick arrays having one $SiO_2$ coated end (the other end having been masked from the treatment). The SiO2 treated end of the chips were dipped into a pH 7.5 sodium phosphate buffer. The buffer immediately wicked through the channels up to the edge of the masked region. The other end of the channels did not wick sample. Also, a control chip prepared in the same way, but without any $SiO_2$ coating, did not wick fluid into any of the channels under the same conditions. These results confirm a low contact angle for the $SiO_2$ treated portion of the chip. It also confirmed that the $SiO_2$ successfully transferred into the high aspect ratio channels that were exposed to the coating.

Various modifications and alterations of this invention will become apparent to those skilled in the art without departing from the scope and spirit of this invention. Although the present invention has been described with reference to preferred embodiments, workers skilled in the art will recognize that changes may be made in form and detail without departing from the spirit and scope of the invention. In addition, the invention is not to be taken as limited to all of the details thereof as modifications and variations thereof may be made without departing from the spirit or scope of the invention.

What is claimed is:

1. A detection article comprising:

at least one polymeric fluid control film layer including an acquisition zone, a detection zone and at least one microstructured major surface including a plurality of embossed microchannels therein that are uniform and regular along substantially each channel length, wherein the microchannels are adapted to draw a fluid sample into the acquisition zone through openings in the microchannels, and to provide fluid flow of the fluid sample from the acquisition zone to the detection zone along the microchannels by spontaneous fluid transport, the detection zone including at least one detection element that facilitates detection of a characteristic of the fluid sample within at least one microchannel of the detection zone.

2. The detection article of claim 1, wherein at least a portion of the film layer is hydrophilic.

3. The detection article of claim 2, wherein the hydrophilic portion of the film layer comprises a hydrophilic material.

4. The detection article of claim 3, wherein the hydrophilic material is poly(vinyl alcohol).

5. The detection article of claim 3, wherein the hydrophilic material comprises a less hydrophilic material combined with an additive to increase hydrophilicity.

6. The detection article of claim 1, wherein the microstructured surface is configured to modify a surface energy of the surface of the fluid control film.

7. The detection article of claim 1, further comprising an intermediate zone extending between the acquisition zone and the detection zone.

8. The detection article of claim 1, wherein the detection zone at least partially overlaps the acquisition zone.

9. The detection article of claim 1, wherein the at least one detection element is associated with at least one microchannel of the film layer.

10. The detection article of claim 9, wherein the at least one detection element is positioned within one of the plurality of microchannels.

11. The detection article of claim 9, wherein the at least one detection element is positioned adjacent one of the plurality of microchannels.

12. The detection article of claim 1, wherein at least one microchannel is comprised of sidewalls that are configured to define the microchannel, and the sidewalls extend continuously from the opening of that microchannel and through the acquisition and detection zones of the detection article with the detection element supported within a continuous microchannel.

13. The detection article of claim 12, further comprising a plurality of microchannels that are each comprised of sidewalls that extend from the opening in that microchannel through the acquisition and detection zones to define a plurality of continuous microchannels that provide discrete fluid transfer paths from one another.

14. The detection article of claim 13, wherein one of the plurality of continuous microchannels supports a different detection element from a detection element that is supported within another of the plurality of continuous microchannels.

15. The detection article of claim 1, wherein the microchannels are defined by sidewalls and a bottom wall between them.

16. The detection article of claim 1, wherein the microchannels are defined by sidewalls that converge together at a bottom of the microchannel.

17. The detection article of claim 1, wherein the microchannels extend continuously over the film layer.

18. The detection article of claim 1, wherein the microchannels extend from one side edge of the film layer to another side edge of the film layer.

19. The detection article of claim 1, wherein the openings in the microchannels are provided at one end of the plurality of microchannels.

20. The detection article of claim 19, wherein the microchannels are configured so as to position the openings of the microchannels across a width of the detection article.

21. The detection article of claim 19, wherein the microchannels are configured so as to position the openings of the microchannels along at least a portion of the length of the detection article.

22. The detection article of claim 1, wherein the openings in the microchannels are provided at a top surface of the microchannels.

23. The detection article of claim 1, wherein the detection zone comprises a plurality of detection elements.

24. The detection article of claim 23, wherein at least one of the plurality of detection elements is associated with each microchannel of the film layer.

25. The detection article of claim 24, wherein at least one of the plurality of detection elements is positioned within one of the plurality of microchannels.

26. The detection article of claim 24, wherein at least one of the plurality of detection elements is positioned adjacent one of the plurality of microchannels.

27. The detection article of claim 23, wherein at least one of the plurality of detection elements is different than at least one other of the detection elements.

28. The detection article of claim 27, wherein each detection element is different than all other detection elements.

29. The detection article of claim 23, wherein at least one of the plurality of detection elements comprises an assay reagent.

30. The detection article of claim 29, wherein the assay reagent is chosen from the group consisting of fluorogenic indicators, chromogenic indicators, electrochemical reagents, agglutination reagents, analyte specific binding agents, amplification agents, enzymes, catalysts, photochromic agents, dielectric compositions, analyte specific reporters, enzyme-linked antibody probes, DNA probes, RNA probes, fluorescent beads, and phosphorescent beads.

31. The detection article of claim 1, wherein the at least one detection element comprises an assay reagent.

32. The detection article of claim 31, wherein the assay reagent is chosen from the group consisting of fluorogenic indicators, chromogenic indicators, electrochemical reagents, agglutination reagents, analyte specific binding agents, amplification agents, enzymes, catalysts, photochromic agents, dielectric compositions, analyte specific reporters, enzyme-linked antibody probes, DNA probes, RNA probes, fluorescent beads, and phosphorescent beads.

33. The detection article of claim 1 wherein the characteristic of the fluid sample to be detected is chosen from the group consisting of color change, fluorescence, luminescence, turbidity, electrical conductivity, voltage change, light absorption, light transmission, pH, and change in physical phase.

* * * * *

UNITED STATES PATENT AND TRADEMARK OFFICE

CERTIFICATE OF CORRECTION

PATENT NO. : 7,223,364 B1 
APPLICATION NO. : 09/612418
DATED : May 29, 2007
INVENTOR(S) : Raymond P. Johnston It is certified that error appears in the above-identified patent and that said Letters Patent is hereby corrected as shown below:

Page 2, Column 2 (U.S. Patent Documents)
Line 2, after "6,238,538 B1" insert -- * --.
Line 3, after "6,240,790 B1" insert -- * --.

Page 2, Column 2 (Other Publications)
Line 7, delete ""Mictrotechnology" and insert -- "Microtechnology --, therefor.
Line 16, delete "MiMicroelectronic" and insert -- Microelectronic --, therefor.
Line 23, delete "Electrochem." and insert -- Electrochem, --, therefor.
Line 25, delete "Plymer" and insert -- Polymer --, therefor.
Line 26, delete "Microdignostic" and insert -- Microdiagnostic --, therefor.

Column 3
Line 42, delete "microptical" and insert -- microoptical --, therefor.

Column 8
Line 19, delete "v-shaped" and insert -- V-shaped --, therefor.

Column 9
Line 56, delete "FIG. 11," and insert -- FIG. 1i, --, therefor.

Column 17
Line 28, after "FIGS." delete "1i-j," and insert -- 1i-1j, --, therefor.

Column 18
Line 41, delete "Shown" and insert -- shown --, therefor.

Column 22
Line 13-24, delete "This viewing region.........layer 235, 265." and insert the same on line 12 (Approx.) after "detected." as continuation of paragraph.

Column 26
Line 5, delete "430:" and insert -- 430 --, therefor.

Column 27
Line 4, delete "calorimetric" and insert -- colorimetric --, therefor.
Line 7, delete "calorimetric" and insert -- colorimetric --, therefor.
Line 24, delete "β-Gal)" and insert -- (β-Gal) --, therefor.
Line 26, delete "(β-Gal)," and insert -- (MUGal), --, therefor.
Line 46-47, delete "systematic" and insert -- Systematic --, therefor.

UNITED STATES PATENT AND TRADEMARK OFFICE

CERTIFICATE OF CORRECTION

PATENT NO. : 7,223,364 B1
APPLICATION NO. : 09/612418
DATED : May 29, 2007
INVENTOR(S) : Raymond P. Johnston It is certified that error appears in the above-identified patent and that said Letters Patent is hereby corrected as shown below:

Column 28
Line 45, delete "stearothermophius," and insert -- stearothermophilus, --, therefor.
Line 54-55, delete "Pseudomonasfluorescens," and insert -- Pseudomonas fluorescens, --, therefor. (Consider space)

Column 29
Line 53, delete "genadotropin," and insert -- gonadotropin, --, therefor.

Column 30
Line 4-5, delete "bronchodialators" and insert -- bronchodilators --, therefor.
Line 15, delete "ticlcoproteins." and insert -- nuclcoproteins. --, therefor.
Line 23, delete "$F_c$and" and insert -- $F_c$ and --, therefor. (Consider Space)

Column 31
Line 25, delete "calorimetric" and insert -- colorimetric --, therefor.

Column 33
Line 59, delete "107" and insert -- $10^7$ --, therefor.

Column 34
Line 22, delete "Rune" and insert -- Run --, therefor.
Line 28, delete "micropippetting" and insert -- micropipetting --, therefor.
Line 33, delete "(eM," and insert -- (3M, --, therefor.
Line 35, delete "cmx6 cm)," and insert -- cmx6 cm), --, therefor. (Consider Space)
Line 43, delete "beating" and insert -- heating --, therefor.
Line 46, after "capillary" insert -- structure --.
Line 53, delete "1, 100" and insert -- 1,100 --, therefor. (Consider Space)
Line 56, delete "Rune" and insert -- Run --, therefor.

Column 35
Line 17, delete "micropippetting" and insert -- micropipetting --, therefor.

Column 36
Line 32, delete "Na2SO4," and insert -- $Na_2SO_4$, --, therefor.
Line 57, delete "calorimetric" and insert -- colorimetric --, therefor.

Column 37
Line 9, delete "myglobin" and insert -- myoglobin --, therefor.
Line 27, delete "MgC12" and insert -- $MgCl_2$ --, therefor.
Line 43, delete "sorbital" and insert -- sorbitol --, therefor.

UNITED STATES PATENT AND TRADEMARK OFFICE

CERTIFICATE OF CORRECTION

PATENT NO. : 7,223,364 B1

APPLICATION NO. : 09/612418
DATED : May 29, 2007
INVENTOR(S) : Raymond P. Johnston It is certified that error appears in the above-identified patent and that said Letters Patent is hereby corrected as shown below:

Column 38
Line 42, delete "(3-times)." and insert -- (3 times). --, therefor.
Line 43, delete "treads" and insert -- threads --, therefor.
Line 46, delete "P, Smith," and insert -- P. Smith, --, therefor.
Line 50, delete "glucoronidase" and insert -- glucuronidase --, therefor.

Column 40
Line 15, delete "Triton" and insert -- TRITON --, therefor.
Line 62, delete "three-types" and insert -- three types --, therefor.

Column 41
Line 11, delete "SiO2" and insert -- $SiO_2$ --, therefor.
Line 13, delete "SiO2" and insert -- $SiO_2$ --, therefor.
Line 39, delete "SiO2" and insert -- $SiO_2$ --, therefor.

Column 44
Line 23, in Claim 33, after "claim 1" insert -- , --.

Signed and Sealed this

Sixth Day of May, 2008

JON W. DUDAS
*Director of the United States Patent and Trademark Office*